United States Patent
Northrop

(10) Patent No.: US 11,420,022 B2
(45) Date of Patent: Aug. 23, 2022

(54) ACTUATING ELEMENTS FOR BENDING MEDICAL DEVICES

(71) Applicants: STRYKER CORPORATION, Kalamazoo, MI (US); STRYKER EUROPEAN OPERATIONS LIMITED, Carrigtwohill (IE)

(72) Inventor: Clay W. Northrop, Salt Lake City, UT (US)

(73) Assignee: Stryker Corporation, Kalamazoo, MI (US)

( * ) Notice: Subject to any disclaimer, the term of this patent is extended or adjusted under 35 U.S.C. 154(b) by 251 days.

(21) Appl. No.: 16/812,210

(22) Filed: Mar. 6, 2020

(65) Prior Publication Data
US 2021/0275779 A1 Sep. 9, 2021

(51) Int. Cl.
*A61M 25/01* (2006.01)
*A61M 25/09* (2006.01)
*A61B 17/12* (2006.01)

(52) U.S. Cl.
CPC .... *A61M 25/0158* (2013.01); *A61M 25/0138* (2013.01); *A61M 25/0155* (2013.01); *A61M 25/09* (2013.01); *A61B 17/12145* (2013.01); *A61M 2205/0266* (2013.01); *A61M 2205/0283* (2013.01); *A61M 2205/0294* (2013.01)

(58) Field of Classification Search
CPC .......... A61M 25/0158; A61M 25/0155; A61M 25/0138; A61M 25/0141; A61M 2025/0161; A61M 25/09; A61M 25/0054; A61M 25/0053; A61M 2025/0058; A61M 25/0013; A61M 2025/0915; A61M 25/0043; A61M 25/0015; A61M 2205/0294; A61M 25/0105; A61M 25/0152; A61M 25/0133
See application file for complete search history.

(56) References Cited

U.S. PATENT DOCUMENTS

| | | | |
|---|---|---|---|
| 5,415,633 A | 5/1995 | Lazarus et al. | |
| 6,447,478 B1 * | 9/2002 | Maynard | F03G 7/065 600/151 |
| 2007/0112331 A1 | 5/2007 | Weber et al. | |
| 2007/0250036 A1 | 10/2007 | Volk et al. | |
| 2009/0264817 A1 * | 10/2009 | Flach | A61N 1/0534 604/95.04 |

(Continued)

OTHER PUBLICATIONS

PCT International Search Report and Written Opinion for International Appln. No. PCT/US2021/021250, Applicant Stryker Corporation, dated Aug. 20, 2021 (11 pages).

*Primary Examiner* — Bhisma Mehta
*Assistant Examiner* — Phoebe Anne Staton
(74) *Attorney, Agent, or Firm* — Vista IP Law Group, LLP

(57) ABSTRACT

A medical device includes: an elongated tube having a wall defining a lumen for the elongated tube, wherein the wall of the elongated tube comprises a first opening; and a first actuating element coupled directly or indirectly to the wall of the elongated tube; wherein at least a part of the first actuating element and the first opening of the wall are located at a same longitudinal position with respect to a longitudinal axis of the elongated tube; and wherein the first actuating element is configured to change size to induce stress and/or displacement at the wall of the elongated tube to cause the elongated tube to bend.

21 Claims, 9 Drawing Sheets

(56) References Cited

U.S. PATENT DOCUMENTS

| | | | |
|---|---|---|---|
| 2010/0069882 A1* | 3/2010 | Jennings | A61M 25/0138 |
| | | | 604/525 |
| 2014/0046250 A1 | 2/2014 | Jain et al. | |
| 2016/0151610 A1* | 6/2016 | Schaffer | C22F 1/006 |
| | | | 29/428 |

* cited by examiner

ACTUATING ELEMENTS FOR BENDING MEDICAL DEVICES

FIELD

The field of the application relates to medical devices, and more specifically, to actuating elements for bending medical devices, and medical devices having such actuating elements.

BACKGROUND

Many medical devices are required to undergo bending during use. For example, a catheter for delivering to and/or for removing substance(s) from inside the patient is required to undergo bending as the catheter is being advanced inside the patient. In many cases, a bending of the catheter can be accomplished using steering wires that are attached to distal end of the catheter. However, use of steering wires to bend catheter may not be desirable as it requires the steering wires to extend from the distal part of the catheter all the way to the proximal end of the catheter. This, in turn, requires the catheter to house the steering wires, preventing the catheter from achieving a certain minimal size. Also, use of steering wires may result in inadvertently moving the catheter by the user while trying to actuate the deflection. In addition, because steering wires create bending of the catheter through tensioning applied from the proximal end of the catheter, use of the steering wires may cause compression in the catheter body, which in turn, may lead to some shortening of the catheter when the catheter is in the deflected or bent state, and may result in a proximal portion of the catheter being straightened. Furthermore, catheters with steering wires may have mechanical issues, such as detachment of steering wires from the catheter body, steering wires getting stuck due to frictional contact with catheter body, etc.

Another type of medical device that requires bending during use is guidewires. Guidewires have been used in the medical field to access passages inside patients. In some cases, it may be desirable for a distal segment of a guidewire to achieve a certain bent shape during use. This allows the distal segment of the guidewire to access a certain passage with specific geometry inside the patient. Generally, such a guidewire has a pre-bent shape, and such pre-bent shape is assumed by the guidewire when the guidewire is in a relaxed configuration (e.g., when no force is imposed on the guidewire). The guidewire may have a relatively straight configuration when confined in a delivery tube. When the guidewire is deployed out of the delivery tube inside a patient, the guidewire then automatically resumes its pre-bent shape. After the guidewire is deployed inside the patient, the curvature of the pre-bent shape of the guidewire is generally not adjustable. A pre-bent guidewire may change shape during use, making it less effective in providing access to the disease treatment site. Further, a pre-bent guidewire may, due to its pre-bent curvature, have a propensity to catch its tip in smaller 'perforator' blood vessels, or on devices such as stents that have been previously deployed or are being deployed.

Another type of medical device that requires bending during use is implants, such as vaso-occlusive devices. In some cases, a vaso-occlusive device may have a certain three-dimensional pre-bent configuration. The vaso-occlusive device may be confined in a delivery tube, and may have a relatively straight configuration when inside the delivery tube. When the vaso-occlusive device is deployed out of the delivery tube inside a patient, the vaso-occlusive device then automatically resumes its three-dimensional pre-bent configuration. After the vaso-occlusive device is deployed inside the patient, the curvature of the pre-bent shape of the vaso-occlusive device is generally not adjustable. Also, the vaso-occlusive device sometimes may be difficult to be advanced within the delivery tube. This is because when the vaso-occlusive device is flexed from its pre-bent shape to a more rectilinear shape when confined inside the delivery tube, the vaso-occlusive device pushes against the inner wall of the delivery tube, creating significant frictional force with the inner wall of the delivery tube.

As such, new techniques for constructing bending medical devices is desirable.

SUMMARY

A medical device includes: an elongated tube having a wall, wherein the wall of the elongated tube comprises a first opening; and a first actuating element located in the first opening of the wall of the elongated tube; wherein the first actuating element in the first opening of the wall is actuatable to induce stress and/or displacement at the wall of the elongated tube to cause the elongated tube to bend.

Optionally, a size of the first actuating element is variable to induce the stress and/or the displacement at the wall of the elongated tube to cause the elongated tube to bend.

Optionally, the size of the actuating element is variable in a direction that is parallel to a longitudinal axis of the elongated tube.

Optionally, the size of the actuating element is variable in a direction that is perpendicular to a longitudinal axis of the elongated tube.

Optionally, the first actuating element is at a first side of the elongated tube, and the elongated tube comprises one or more slots or other structural feature(s) at a second side of the elongated tube, the second side being opposite from the first side.

Optionally, the first actuating element is configured to expand, to contract, or to both expand and to contract.

Optionally, the first actuating element is configured to expand within the first opening of the wall to cause the elongated tube to bend in a first direction, and wherein the first actuating element is configured to contract within the opening of the wall to cause the elongated tube to bend in a second direction that is opposite from the first direction.

Optionally, the wall of the elongated tube comprises a first linkage and a second linkage coupled with respective opposite sides of the first actuating element.

Optionally, the first actuating element is configured to apply opposite forces towards the first and second linkages to induce the stress and/or the displacement at the wall of the elongated tube.

Optionally, the first linkage comprises a first part of the wall, and the second linkage comprises a second part of the wall, the first and second parts of the wall formed by laser-cutting, etching, or removing material from, the elongated tube.

Optionally, the first actuating element comprises a piezo element, a balloon, an electroactive polymer, or a shape-memory element.

Optionally, the first actuating element is actuatable in response to electrical energy, radiofrequency energy, temperature change, delivery of fluid, or pressure.

Optionally, the wall of the elongated tube comprises a second opening, and wherein the medical device further comprises a second actuating element located in the second opening of the wall of the elongated tube.

Optionally, the first actuating element and the second actuating element are located on a same side of the elongated tube.

Optionally, the first actuating element and the second actuating element are located on different respective sides of the elongated tube.

Optionally, the first actuating element is configured to cause the elongated tube to bend in a first direction, and the second actuating element is configured to cause the elongated tube to bend in a second direction that is different from the first direction.

Optionally, the elongated tube is a part of a catheter.

Optionally, the elongated tube is a part of a guidewire.

Optionally, the elongated tube is a part of an implant.

Optionally, the implant is configured to deform plastically.

Optionally, the first actuating element and/or the elongated tube is configured to deform elastically.

Optionally, the first actuating element and/or the elongated tube is configured to deform plastically.

A medical device includes: an elongated tube having a wall defining a lumen for the elongated tube, wherein the wall of the elongated tube comprises a first opening; and a first actuating element coupled directly or indirectly to the wall of the elongated tube; wherein at least a part of the first actuating element and the first opening of the wall are located at a same longitudinal position with respect to a longitudinal axis of the elongated tube; and wherein the first actuating element is configured to change size to induce stress and/or displacement at the wall of the elongated tube to cause the elongated tube to bend.

Optionally, the first actuating element is configured to alter a cross-sectional dimension of the first opening to induce the stress and/or the displacement at the wall of the elongated tube.

Optionally, the first actuating element is actuatable, and is located in the first opening of the wall of the elongated tube.

Optionally, the wall of the elongated tube comprises a first linkage and a second linkage coupled with respective opposite sides of the first actuating element.

Optionally, the first actuating element is configured to apply opposite forces towards the first and second linkages to induce the stress and/or the displacement at the wall of the elongated tube.

Optionally, the wall of the elongated tube comprises a second opening, and wherein the medical device further comprises a second actuating element located in the second opening of the wall of the elongated tube.

Optionally, the first actuating element is configured to cause the elongated tube to bend in a first direction, and the second actuating element is configured to cause the elongated tube to bend in a second direction that is the same as, or different from, the first direction.

Optionally, the first actuating element extends across the first opening of the wall of the elongated tube.

Optionally, the first actuating element is coupled to an exterior surface of the elongated tube.

Optionally, the first actuating element is coupled to an interior surface of the elongated tube.

Optionally, the wall of the elongated tube further comprises a second opening, and wherein the first actuating element also extends across the second opening of the wall of the elongated tube.

Optionally, the elongated tube comprises a distal end and a proximal end, and wherein the first actuating element is located between the distal end and the proximal end of the elongated tube.

Optionally, the medical device further includes a structural member coupled between opposite sides of the first opening, wherein the first actuating element is located in the lumen of the elongated tube, and is configured to apply a force towards the structural member.

Optionally, the structural member has a length that is longer than a dimension of the opening, Optionally, the first actuating element is configured to apply the force in a direction that is perpendicular to the longitudinal axis of the elongated tube.

Optionally, the first actuating element is at a first side of the elongated tube, and the elongated tube comprises one or more slots, or other structural feature(s), at a second side of the elongated tube, the second side being opposite from the first side.

Optionally, the first actuating element is configured to expand, to contract, or to both expand and to contract.

Optionally, the first actuating element comprises a piezo element, a balloon, an electroactive polymer, or a shape-memory element.

Optionally, the first actuating element is actuatable in response to electrical energy, radiofrequency energy, temperature change, delivery of fluid, or pressure.

Optionally, the elongated tube is a part of a catheter, a part of a guidewire, or a part of an implant.

Optionally, the implant is configured to deform plastically.

Optionally, the first actuating element and/or the elongated tube is configured to deform elastically.

Optionally, the first actuating element and/or the elongated tube is configured to deform plastically.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
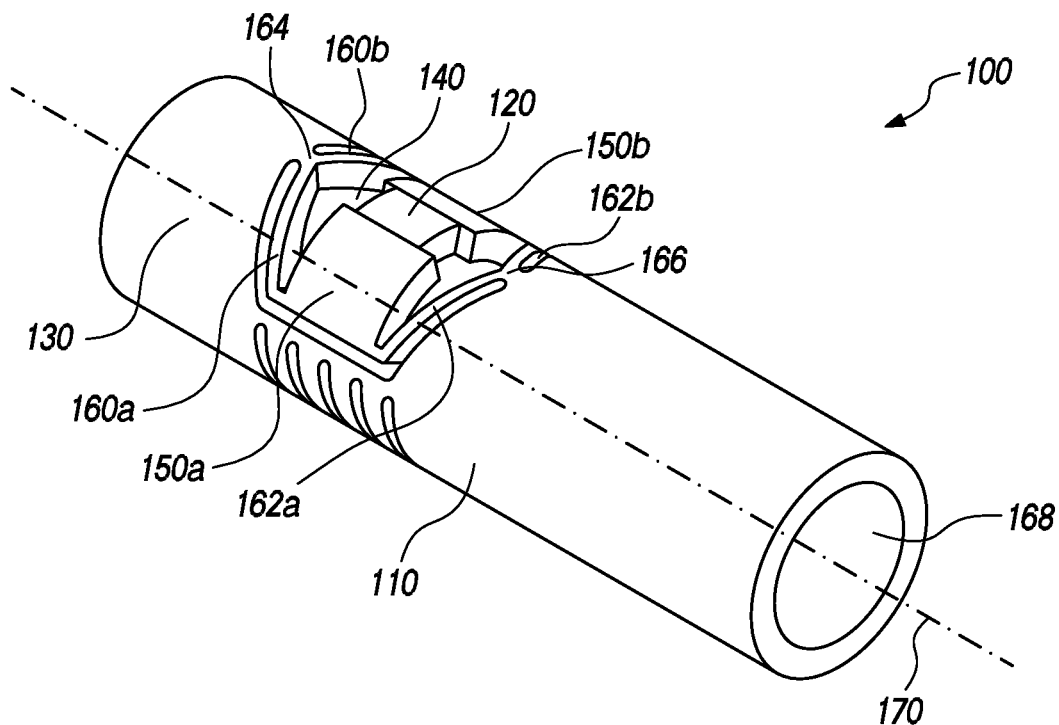
FIG. 1 illustrates a medical device having a tube and an actuating element for bending the tube in accordance with some embodiments.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Figure 2:
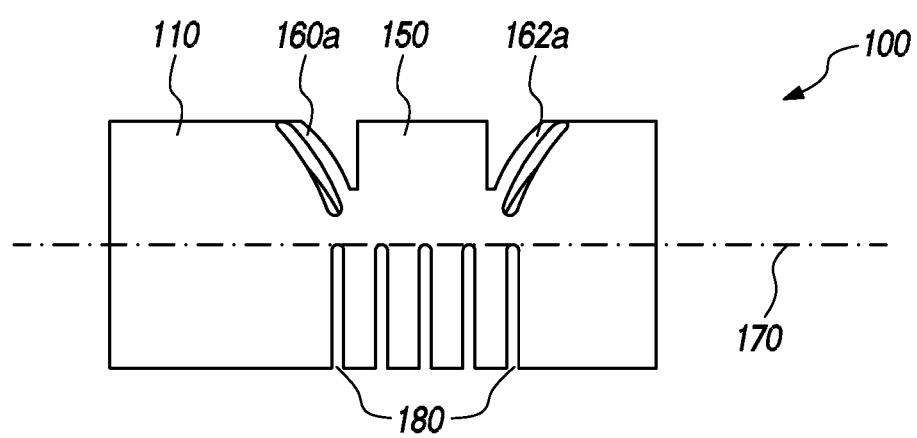
FIG. 2 illustrates a side view of the medical device of FIG. 1.

FIGS. 1-2 illustrate a medical device 100 having an elongated tube 110 and an actuating element 120 for bending the elongated tube 110 in accordance with some embodiments. The elongated tube 110 has a wall 130 defining a lumen 168 for the elongated tube 110, wherein the wall 130 of the elongated tube comprises a first opening 140. The medical device 100 also includes the actuating element (first actuating element) 120 located in the first opening 140 of the wall 130 of the elongated tube 110. The first actuating element 120 in the first opening 140 of the wall 130 is actuatable to induce stress and/or displacement at the wall 130 of the elongated tube 110 to cause the elongated tube 110 to bend.

In the illustrated embodiments, a size of the first actuating element 120 is variable to induce the stress and/or displacement at the wall 130 of the elongated tube 110 to cause the elongated tube 110 to bend. The size of the actuating element 120 may be variable in a direction that is parallel to a longitudinal axis 170 of the elongated tube 130, variable in a direction that is perpendicular to the longitudinal axis 170 of the elongated tube 130, or variable in both the direction that is parallel to the longitudinal axis 170 and the direction that is perpendicular to the longitudinal axis 170.

In some embodiments, the first actuating element 120 is configured to expand in the first opening 140 of the wall 130 of the elongated tube 110 to cause the elongated tube 110 to bend. In other embodiments, the first actuating element 120 is configured to contract in the first opening 140 of the wall 130 of the elongated tube 110 to cause the elongated tube 110 to bend. In further embodiments, the first actuating element 120 is configured to both expand and to contract. In such cases, expansion of the first actuating element 120 will cause the elongated tube 110 to bend in a first direction, and contraction of the first actuating element 120 will cause the elongated tube to bend in a second direction that is opposite from the first direction.

As shown in FIG. 1, the wall 130 of the elongated tube 110 comprises a first linkage 150a and a second linkage 150b coupled with respective opposite sides of the first actuating element 120. The first linkage 150a includes a first structural member 160a and a second structural member 162a configured to transfer forces caused by the first actuating element 120 into the wall 130 of the elongated tube 110. The first structural member 160a and the second structural member 162a both connect to junction member 164, which is configured to transfer forces from the first and second structural members 160a, 162a into the wall 130 of the elongated tube 110. Similarly, the second linkage 150b includes a first structural member 160b and a second structural member 162b configured to transfer forces caused by the first actuating element 120 into the wall 130 of the elongated tube 110. The first structural member 160b and the second structural member 162b both connect to junction member 166, which is configured to transfer forces from the first and second structural members 160b, 162b into the wall 130 of the elongated tube 110.

In the illustrated embodiments, first linkage 150a comprises a first part of the wall 130, and the second linkage 150b comprises a second part of the wall 130. The first and second parts of the wall 130 constituting the first and second linkages 150a, 150b may be formed by laser-cutting or otherwise removing material from the elongated tube 110. Also, the junction members 164, 166 comprise parts of the wall 130 of the elongated tube 110. The junction members 164, 166 may also be formed by laser-cutting or otherwise removing material from the elongated tube 110.

Figure 3:
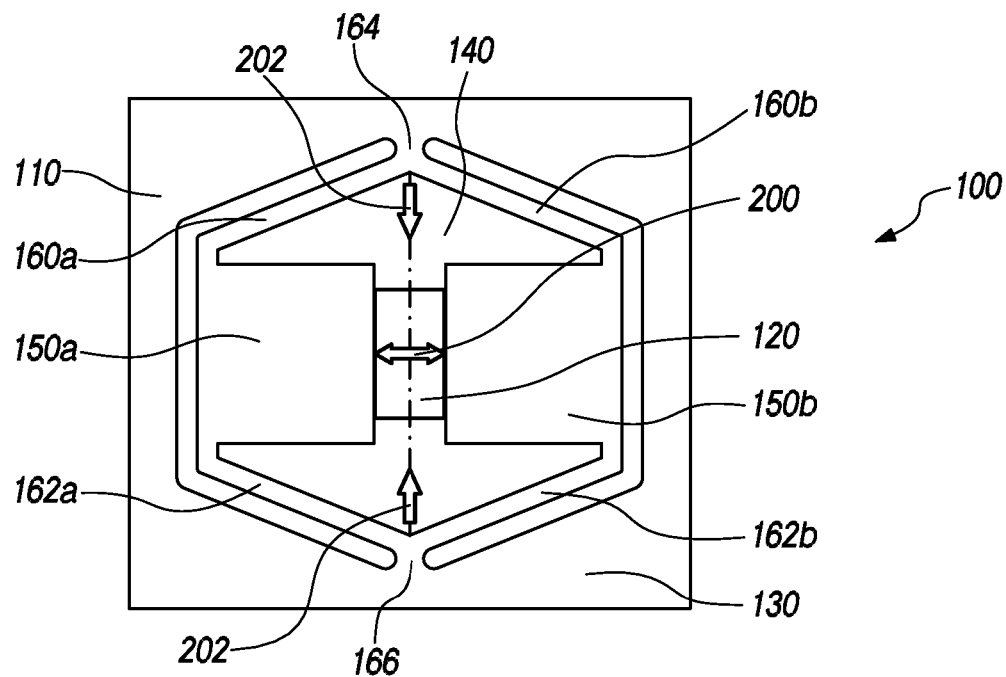
FIG. 3 illustrates a force and movement diagram for the medical device of FIG. 1.

In the illustrated embodiments, the first actuating element 120 is configured to apply opposite forces towards the first and second linkages 150a, 150b to induce stress and/or displacement at the wall 130 of the elongated tube 110. FIG. 3 illustrates a force and movement diagram for the medical device of FIG. 1. As represented by the arrow 200 in the figure, the first actuating element 120 may be configured to expand and/or contract within the first opening 140 of the wall 130 of the elongated tube 110. Expansion of the first actuating element 120 will push the first and second linkages 150a, 150b away from each other, causing tension in the first and second structural members 160a, 162a of the first linkage 150a, and also tension in the first and second structural members 160b, 162b of the second linkage 150b. This, in turn, will cause the junction members 164, 166 to be pulled towards each other (as represented by arrows 202), thereby shortening the distance between the junction members 164, 166. As a result, the elongated tube 110 will bend towards the side of the elongated tube 110 where the first actuating element 120 is located.

Conversely, contraction of the first actuating element 120 will pull the first and second linkages 150*a*, 150*b* towards each other, causing compression in the first and second structural members 160*a*, 162*a* of the first linkage 150*a*, and also compression in the first and second structural members 160*b*, 162*b* of the second linkage 150*b*. This, in turn, will cause the junction members 164, 166 to be pushed away from each other, thereby lengthening the distance between the junction members 164, 166. As a result, the elongated tube 110 will bend towards the side of the elongated tube 110 that is opposite from the side where the first actuating element 120 is located.

It should be noted that the technique of changing a distance between two points at the wall 130 of the elongated tube 110 using the actuating element 120 is advantageous because a small movement or displacement by the actuating element 120 can create a large deflection at the tip of the elongated tube 110. Linkages and structural members may be configured to amplify the displacement of actuating element 120 to differing degrees, by modifying the angle of the structural members relative to the axis of expansion or contraction of the actuating element.

As shown in FIG. 1-2, the first actuating element 120 is at a first side of the elongated tube 110, and the elongated tube 110 also comprises one or more slots 180, or other structural feature(s), at a second side of the elongated tube 110, the second side being opposite from the first side. The slot(s) 180 or the structural feature(s) of the elongated tube 110 allows the elongated tube 110 to be more easily bent by the first actuating element 120.

The first actuating element 120 may be implemented using different techniques in different embodiments. In some embodiments, the first actuating element 120 may be a piezoelectric (piezo) element. In such cases, the medical device 100 may also include electrical wires connected to the first actuating element 120 for applying energy (e.g., current, voltage, etc.) to drive the piezoelectric element, causing the piezoelectric element to change size and/or shape. In other embodiments, the first actuating element 120 may be a shape-memory (e.g., Nitinol or NiTi) element. In such cases, the medical device 100 may include electrical wires connected to the shape-memory element for applying a current to cause the shape-memory element to change size and/or shape. In some embodiments, the shape-memory element may heat up due to resistive heating caused by the current, wherein the heating will cause the shape-memory element to change size and/or shape. In other embodiments, other means of changing the temperature of the shape-memory element may be employed, such as delivery of fluid to the element at an elevated temperature, contact by the element or proximity of the element to an elevated-temperature surface, or use of radio-frequency energy to induce eddy currents in the shape-memory element, thus elevating its temperature and creating a change in shape. In further embodiments, the first actuating element 120 may be made from one or more electroactive polymers, which can exhibit a change in size and/or shape when stimulated by an electric field or current. In such cases, the medical device 100 may include electrical wires connected to the first actuating element 120 for applying a current to cause the first actuating element 120 to change size and/or shape. In still further embodiments, the first actuating element 120 may be a balloon. In such cases, the medical device 100 may include fluid delivery channel(s) for inflating the balloon to cause the balloon to change size and/or shape.

In the above examples, the first actuating element 120 is described as being actuatable in response to electrical energy (e.g., current or voltage), or fluidic energy. In other embodiments, the first actuating element 120 may be actuatable in response to radiofrequency energy. In such cases, the first actuating element 120 may include a receiver configured to receive radiofrequency energy, and a converter configured to convert the radiofrequency energy into electrical energy (e.g., current or voltage). The electrical energy (e.g., current or voltage) may then be utilized by the first actuating element 120 to change its size and/or shape. In some embodiments, the radiofrequency energy may be one or more radiofrequency signals transmitted from a controller. The controller may include a user interface configured to allow a user to provide inputs for provisioning the radiofrequency signals. In further embodiments, the actuating element 120 is actuatable in response to other form of energies, such as light energy, ultrasound energy, etc., that are not mechanical energy associated with tensioning of a steering wire. Also, in some embodiments, the actuating element 120 may be actuatable in response to delivery of fluid that provides volume displacement and/or fluid pressure. In other embodiments, the actuating element 120 may be actuatable in response to mechanical displacement and/or mechanical pressure.

In the above embodiments, the medical device 100 has one actuating element (first actuating element) 120. In other embodiments, the medical device 100 may have a plurality of actuating elements 120. For example, in other embodiments, instead of having one actuating element 120 in the opening 140 of the wall, the medical device 100 may have multiple actuating elements 120 stacked in the opening 140. Such configuration allows differing degrees of deflection by selectively actuating one or multiple one of the actuating elements simultaneously.

Figure 4A:
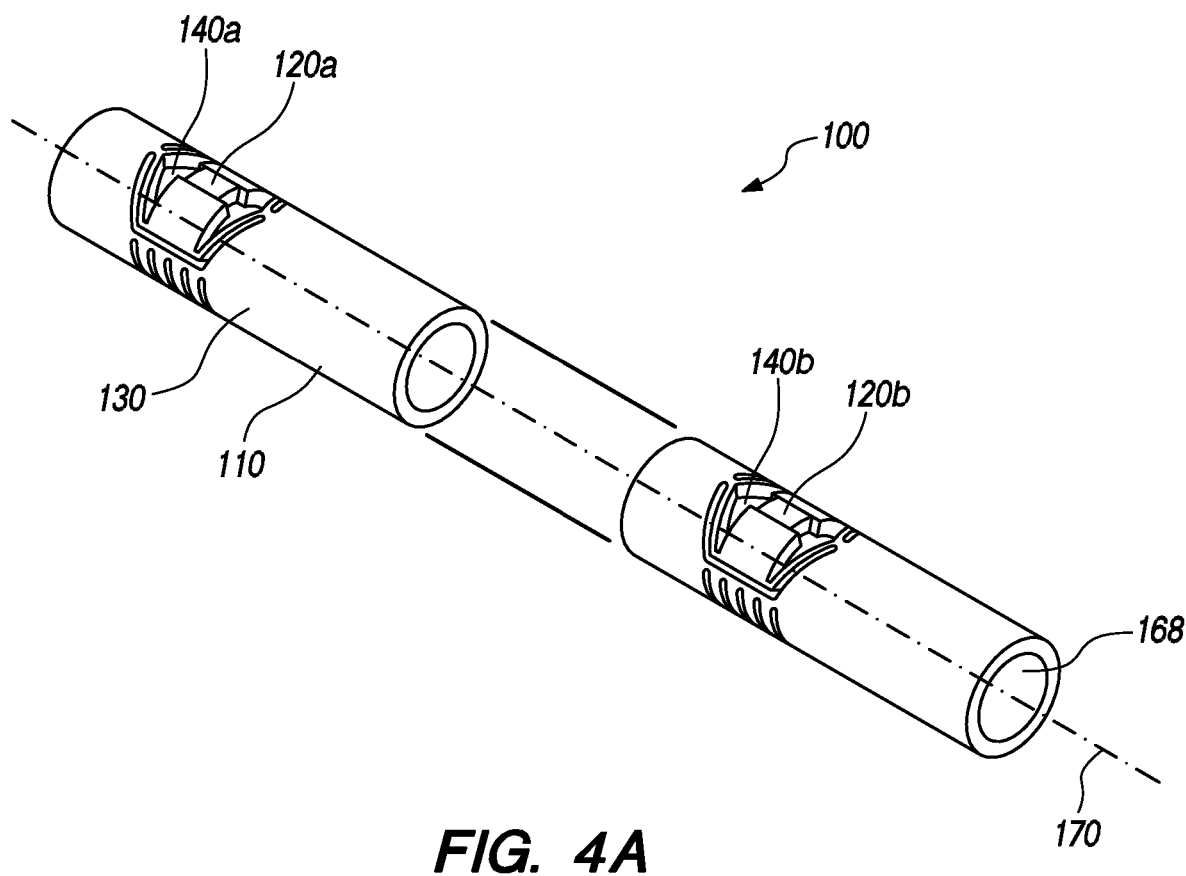
FIG. 4A illustrates a medical device having a tube and a plurality of actuating elements for bending the tube in accordance with other embodiments.

In further embodiments, instead of having the multiple actuating elements 120 all located in the same opening 140 of the wall 130, the multiple actuating elements 120 may be located in different respective openings 140. For example, as shown in FIG. 4A, in other embodiments, the wall 130 of the elongated tube 110 may include a first opening 140*a* and a second opening 140*b*. In such cases, the medical device 100 comprises a first actuating element 120*a* located in the first opening 140*a*, and a second actuating element 120*b* located in the second opening 140*b* of the wall 130 of the elongated tube 110. As shown in the figure, the first actuating element 120*a* and the second actuating element 120*b* are both located on a same side of the elongated tube 110. This configuration allows the actuating elements 120*a*, 120*b* to bend different segments of the elongated tube 110 towards the same side of the elongated tube 110 (i.e., in a same bending plane).

Figure 4B:
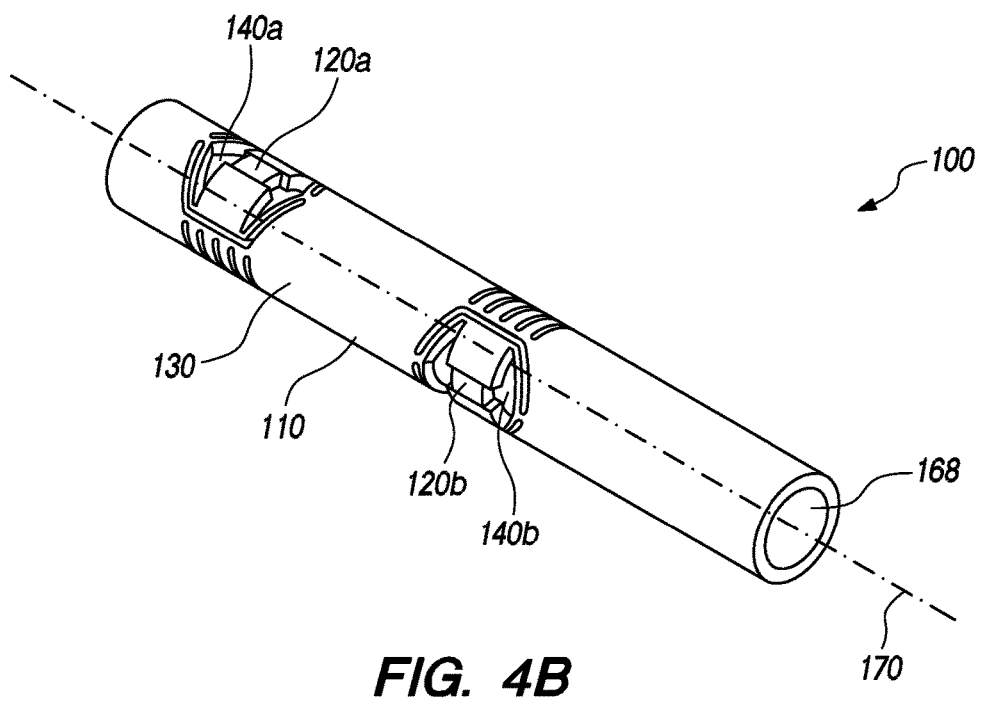
FIG. 4B illustrates a medical device having a tube and a plurality of actuating elements for bending the tube in accordance with other embodiments.

In other embodiments, the first actuating element 120*a* and the second actuating element 120*b* may be located on different respective sides of the elongated tube 110 (FIG. 4B). This configuration allows the actuating elements 120*a*, 120*b* to bend the elongated tube 110 in different bending planes. For example, the first actuating element 120*a* may be configured to cause the elongated tube 110 to bend in a first direction in a first bending plane, and the second actuating element 120*b* may be configured to cause the elongated tube 110 to bend in a second direction (in a second bending plane) that is different from the first direction.

Figure 4C:
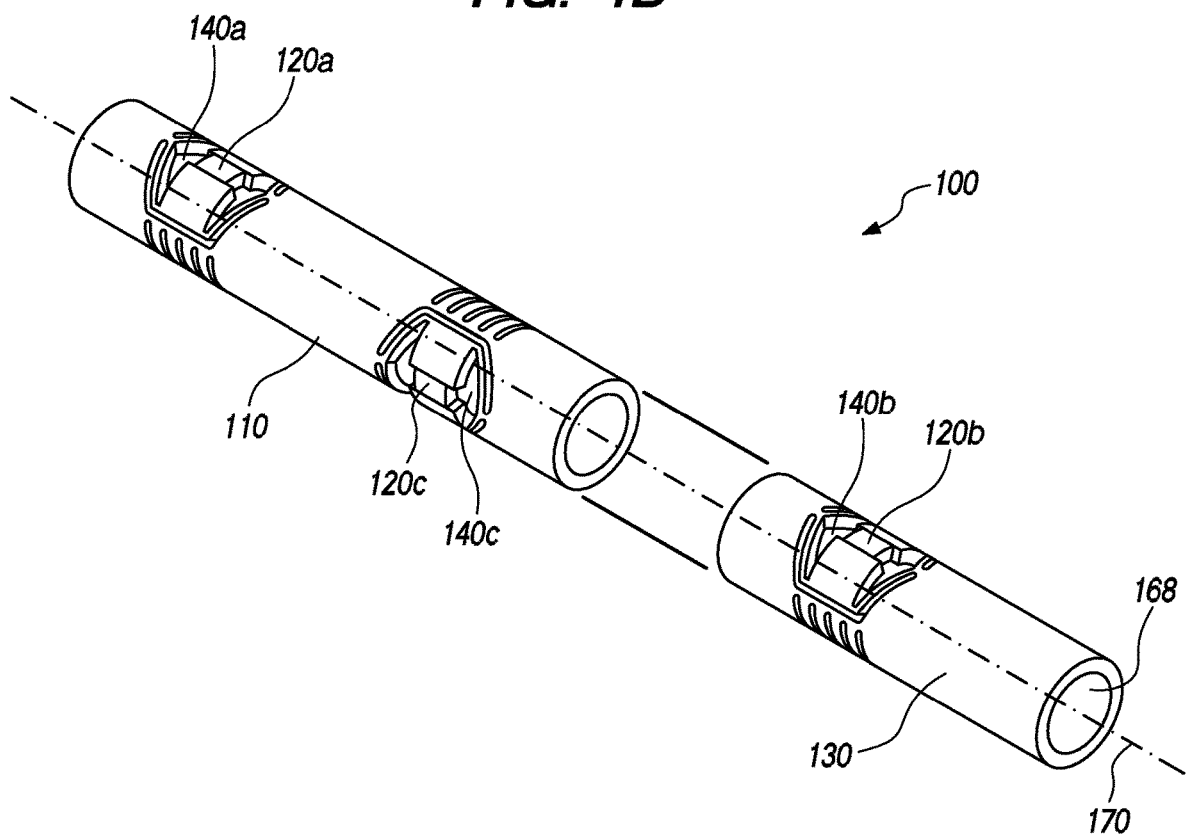
FIG. 4C illustrates a medical device having a tube and a plurality of actuating elements for bending the tube in accordance with other embodiments.

In further embodiments, the medical device 100 may include more than two actuating elements 120. FIG. 4C illustrates a medical device 100 having an elongated tube 110 and a plurality of actuating elements 120 for bending the elongated tube 110 in accordance with other embodiments.

The medical device 100 is the same as that shown in FIG. 4A, except that the wall 130 of the elongated tube 100 further includes a third opening 140c, and a third actuating element 120c located in the third opening 140c. The third actuating element 120c has the same configuration as that of the first actuating element 120a. As shown in the figure, the first and second actuating elements 120a, 120b are located at the same circumferential position with respect to the longitudinal axis 170 of the elongated tube 110, and the third actuating element 120c is located at a different circumferential position from that of the first and second actuating elements 120a, 120b with respect to the longitudinal axis 170. Such configuration allows the first and second actuating elements 120a, 120b to bend the elongated tube 110 in a first bending plane, and also allows the third actuating element 120c to bend the elongated tube 110 in a second bending plane that is different from the first bending plane. The first and second actuating elements 120a, 120b allow bending of different segments along the length of the elongated tube 110. In further embodiments, the medical device 100 may optionally include a fourth opening and a fourth actuating element located in the fourth opening. The third and fourth actuating elements may be located at the same circumferential position with respect to the longitudinal axis 170 of the elongated tube 110. This allows the third and the fourth actuating elements to bend different segments of the elongated tube 110 in the same bending plane.

Figure 5A:
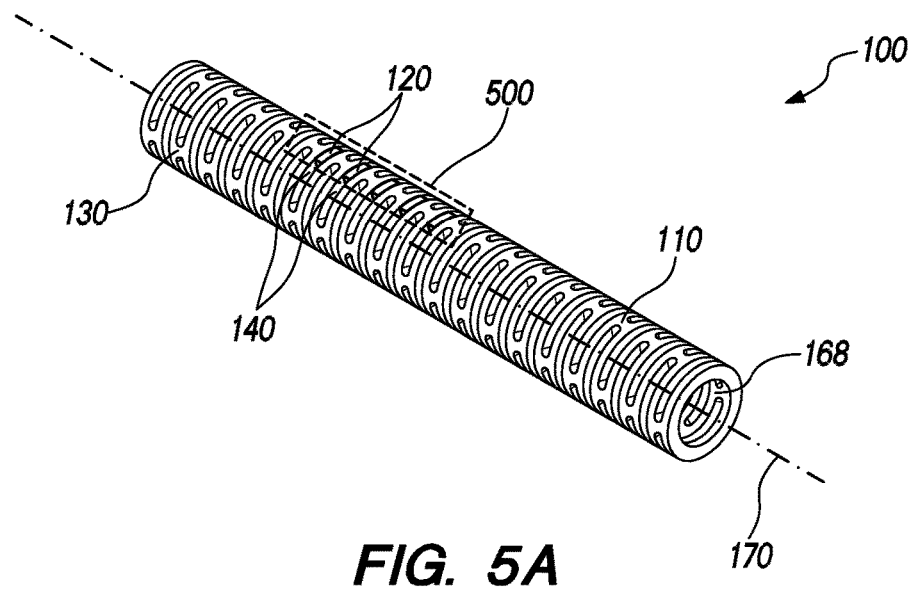
FIG. 5A illustrates a medical device having a tube and a plurality of actuating elements for bending the tube in accordance with other embodiments.

In the above embodiments, the medical device 100 is illustrated as having an elongated tube 110 that has a continuous surface along the longitudinal axis 170 of the elongated tube 110. In other embodiments, the elongated tube 110 of the medical device 100 may be a slotted tube with a plurality of slots along the longitudinal axis 170 of the elongated tube 110. FIG. 5A illustrates a medical device 100 having a tube 110 and a plurality of actuating elements 120 for bending the tube in accordance with other embodiments. As shown in the figure, the actuating elements 120 are located in respective openings 140 defined by the wall 130 of the elongated tube 110. The openings 140 are elongated slots extending circumferentially with respect to the longitudinal axis 170 of the elongated tube 110. The slots divide the elongated tube 110 into a plurality of ring-like elements aligned along the longitudinal axis 170. In the illustrated embodiments, the actuating elements 120 are in a group 500 and are aligned longitudinally in a series. Each actuating element 120 may be implemented using any of the techniques described with reference to the embodiments of FIG. 1. Unlike the embodiments of FIG. 1, the elongated tube 110 of FIG. 5A does not include the linkages 160a, 160b, 162a, 162b. Instead, in the embodiments of FIG. 5A, each actuating element 120 directly abuts two adjacent ring-like elements of the elongated tube 110, and is configured to change size to directly exert opposite forces against the two adjacent ring-like elements of the elongated tube 110.

During use, one or more of the actuating elements 120 may be actuated to cause the elongated tube 110 to bend. In particular, each actuating element 120 is configured to change size to thereby cause the elongated tube 110 to bend. The actuating element 120 may expand to increase a dimension (measured along the longitudinal axis 170) of the opening 140 on one side of the elongated tube 110, contract to decrease the dimension of the opening 140, or both expand and to contract. When the actuating element 120 expands to increase the dimension of the opening 140 (or spacing between adjacent ring-like elements of the elongated tube 110) on one side of the elongated tube 110, it causes a lengthening of that side of the elongated tube 110, thereby bending the elongated tube 110 in a direction that is opposite to that side of the elongated tube 110. On the other hand, when the actuating element 120 contracts to decrease the dimension of the opening 140 (or spacing between adjacent ring-like elements of the elongated tube 110) on one side of the elongated tube 110, it causes a shortening of that side of the elongated tube 110, thereby bending the elongated tube 110 in a direction that is towards that side of the elongated tube 110. The actuating element 120 may be implemented using any of the techniques described with reference to the embodiments of FIG. 1.

In some cases, a degree of bending of the elongated tube 110 may correspond with a number of the actuating elements 120 being actuated. For example, if slight bending of the elongated tube 110 is desired, then only one of the actuating elements 120 may be actuated. On the other hand, if more bending of the elongated tube 110 (e.g., higher curvature) is desired, then more actuating elements 120 may be actuated. In the illustrated embodiments, because the actuating elements 120 are aligned on the same side of the elongated tube 110, actuation of one or more of the actuating elements 120 will cause the elongated tube 110 to bend in the same bending plane.

In the above embodiments, the medical device 100 has one group 500 of actuating elements 120. In other embodiments, the medical device 100 may have a plurality of groups 500 of actuating elements 120.

Figure 5B:
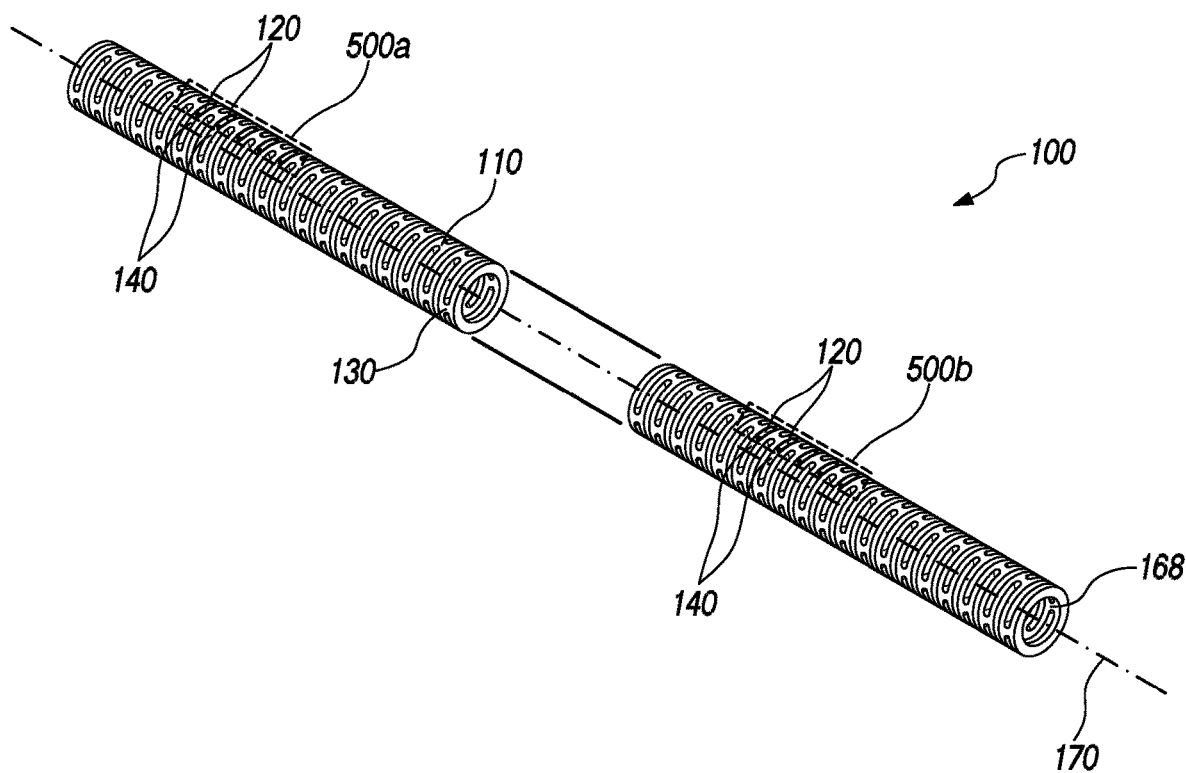
FIG. 5B illustrates a medical device having a tube and a plurality of actuating elements for bending the tube in accordance with other embodiments.

For example, as shown in FIG. 5B, in other embodiments, the medical device 100 comprises a first group 500a of actuating element 120 located in respective openings 140, and a second group 500b of actuating element 120 located in respective openings of the wall 130 of the elongated tube 110. As shown in the figure, the first group 500a of actuating elements 120 and the second group 500b of actuating elements 120 are both located on a same side of the elongated tube 110. This configuration allows the two groups 500a, 500b of actuating elements 120 to bend different segments of the elongated tube 110 towards the same side of the elongated tube 110 (i.e., in a same bending plane).

Figure 5C:
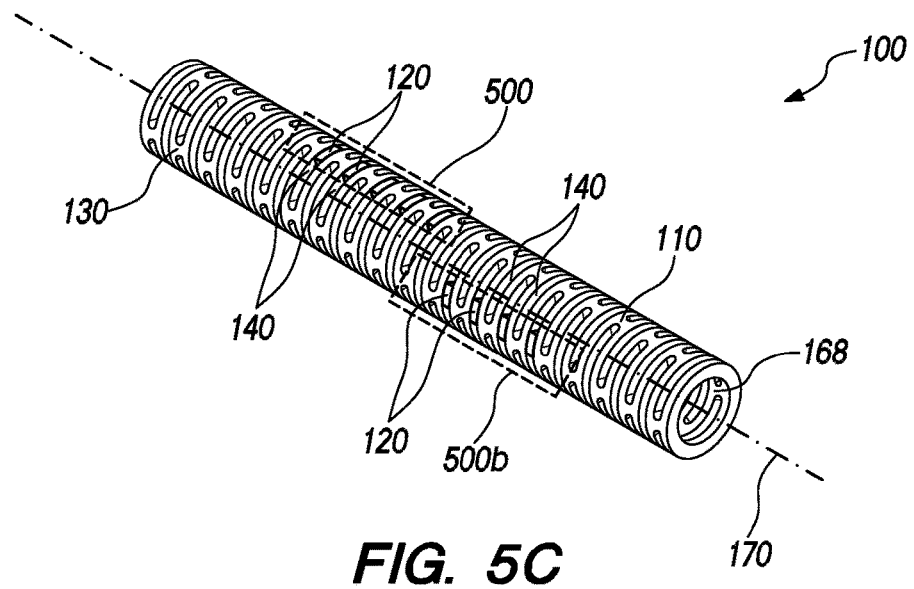
FIG. 5C illustrates a medical device having a tube and a plurality of actuating elements for bending the tube in accordance with other embodiments.

In other embodiments, the first group 500a of actuating elements and the second group 500b of actuating elements 120 may be located on different respective sides of the elongated tube 110 (FIG. 5C). This configuration allows the groups 500a, 500b of actuating elements 120 to bend the elongated tube 110 in different bending planes. For example, the first group 500a of actuating elements 120 may be configured to cause the elongated tube 110 to bend in a first direction in a first bending plane, and the second group 500b of actuating element 120 may be configured to cause the elongated tube to bend in a second direction (in a second bending plane) that is different from the first direction.

Figure 5D:
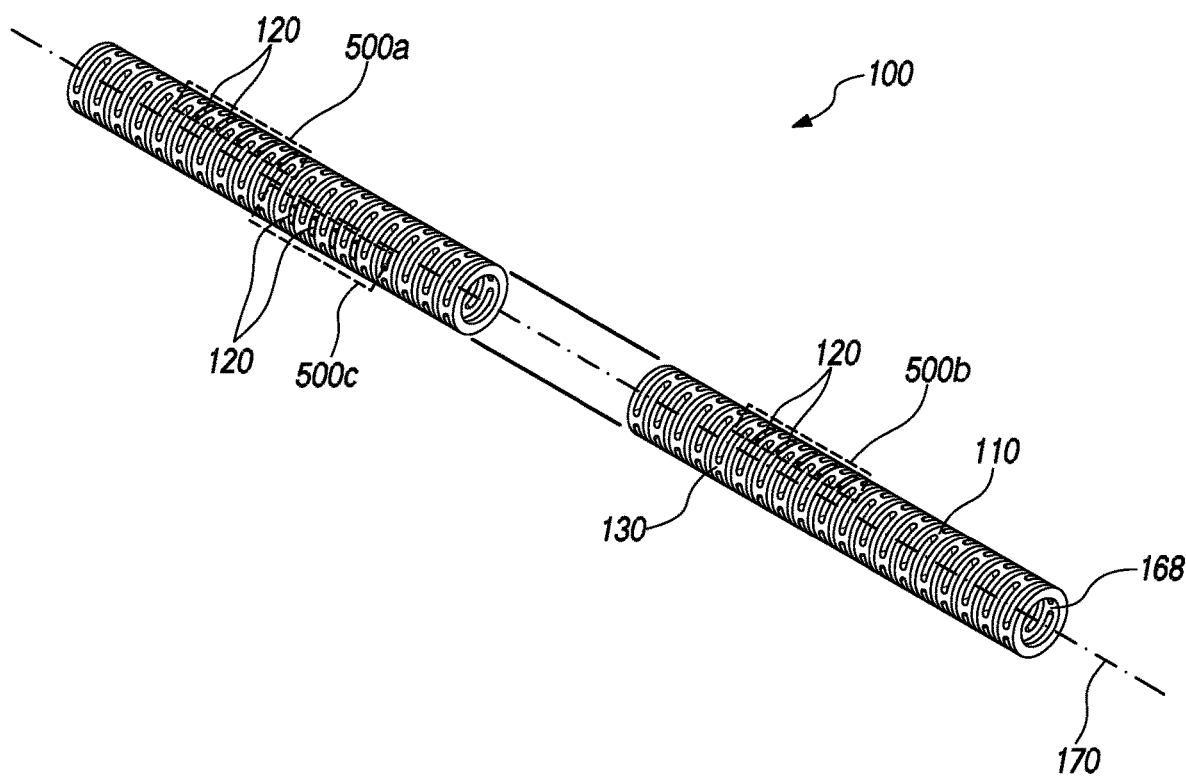
FIG. 5D illustrates a medical device having a tube and a plurality of actuating elements for bending the tube in accordance with other embodiments.

In further embodiments, the medical device 100 may include more than two groups 500 of actuating elements 120. FIG. 5D illustrates a medical device 100 having an elongated tube 110 and a plurality of actuating elements 120 for bending the elongated tube 110 in accordance with other embodiments. The medical device 100 is the same as that shown in FIG. 5B, except that the medical device 100 further includes a third group 500c of actuating elements 120. The third group 500c of actuating elements 120 has the same configuration as that of the first group 500a of actuating elements 120. As shown in the figure, the first and second groups 500a, 500b of actuating elements 120 are located at the same circumferential position with respect to the longitudinal axis 170 of the elongated tube 110, and the third group 500c of actuating elements 120 is located at a different circumferential position from that of the first and second groups 500a, 500b of actuating elements 120 with respect to the longitudinal axis 170. Such configuration allows the first and second groups 500a, 500b of actuating elements 120 to bend the elongated tube 110 in a first bending plane, and also allows the third group 500c of actuating elements 120 to bend the elongated tube 110 in a second bending plane that is different from the first bending plane. The first and second groups 500a, 500b of actuating elements 120 allow bending of different segments along the length of the elongated tube 110. In further embodiments, the medical device 100 may optionally include a fourth group of actuating elements. The third and fourth groups of actuating elements 120 may be located at the same circumferential position with respect to the longitudinal axis 170 of the elongated tube 110. This allows the third and the fourth groups of actuating elements 120 to bend different segments of the elongated tube 110 in the same bending plane.

In the above embodiments, the actuating elements 120 are described as being located in openings 140 of the wall 130 of the elongated tube 110. In other embodiments, one or more actuating elements 120 may be located outside the openings 140 of the wall 130 of the elongated tube 110.

Figure 6A:
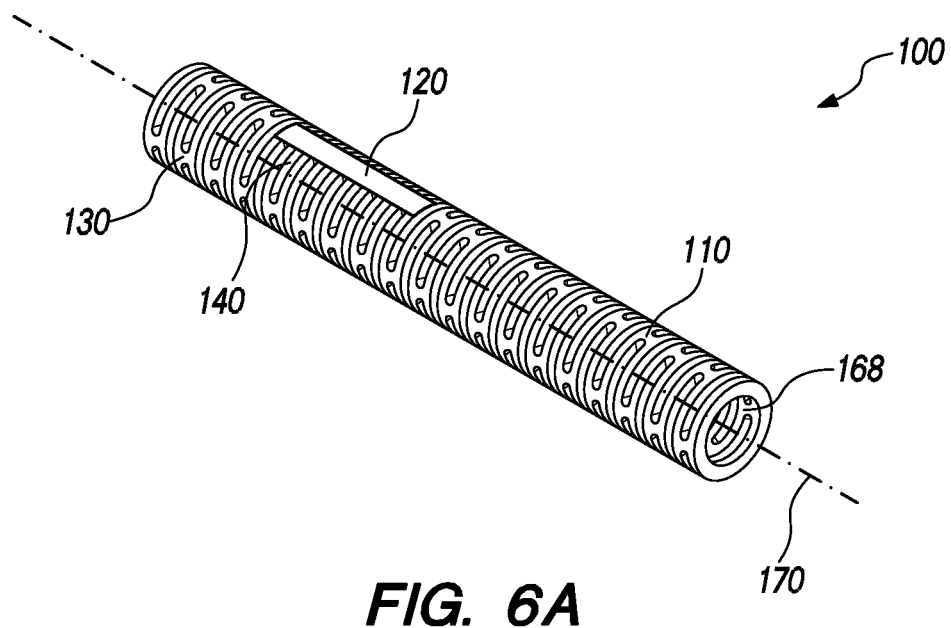
FIG. 6A illustrates a medical device having a tube and an actuating element for bending the tube in accordance with other embodiments.

FIG. 6A illustrates a medical device having an elongated tube 110 and an actuating element 120 for bending the elongated tube 110 in accordance with other embodiments. In the illustrated embodiments, the elongated tube 110 has a plurality of openings 140 that are in the form of elongated slots extending circumferentially with respect to the longitudinal axis 170 of the elongated tube 110. The slots divide the elongated tube 110 into a plurality of ring-like elements aligned along the longitudinal axis 170. As shown in the figure, the actuating element 120 is coupled to an exterior surface of the elongated tube 110, and extends across multiple ones of the openings 140. In other embodiments, the actuating element 120 may extend across only one of the openings 140.

The actuating element 120 is configured to change size to thereby cause the elongated tube 110 to bend. In particular, the actuating element 120 may expand to increase a dimension (measured along the longitudinal axis 170) of the opening 140 on one side of the elongated tube 110, contract to decrease the dimension of the opening 140, or both expand and to contract. When the actuating element 120 expands to increase the dimension of the opening 140 on one side of the elongated tube 110, it causes a lengthening of that side of the elongated tube 110, thereby bending the elongated tube 110 in a direction that is opposite to that side of the elongated tube 110. On the other hand, when the actuating element 120 contracts to decrease the dimension of the opening 140 on one side of the elongated tube 110, it causes a shortening of that side of the elongated tube 110, thereby bending the elongated tube 110 in a direction that is towards that side of the elongated tube 110. The actuating element 120 may be implemented using any of the techniques described with reference to the embodiments of FIG. 1.

Figure 6B:
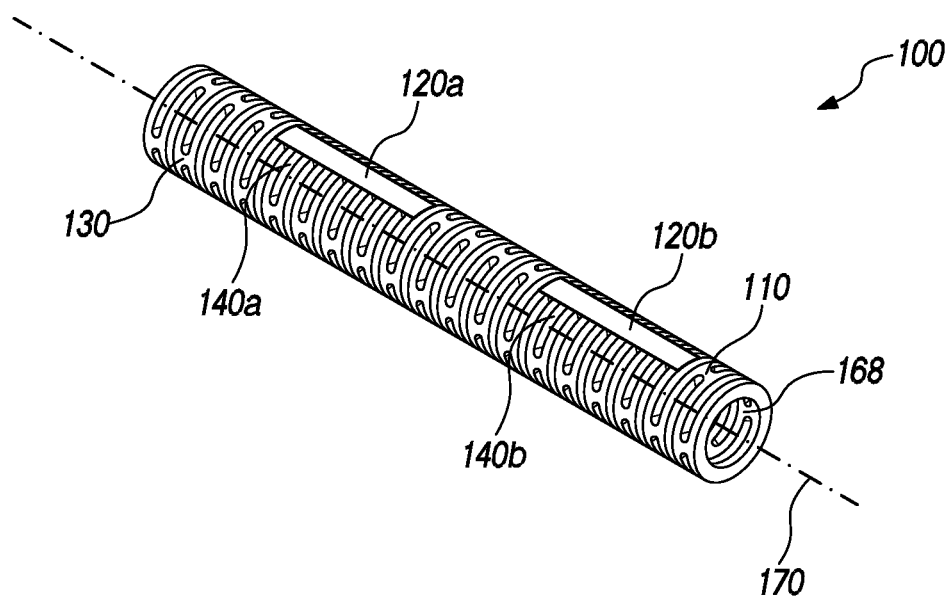
FIG. 6B illustrates a medical device having a tube and a plurality of actuating elements for bending the tube in accordance with other embodiments.

In the above embodiments of FIG. 6A, the medical device 100 has one actuating element (first actuating element) 120. In other embodiments, the medical device 100 may have a plurality of actuating elements 120. For example, as shown in FIG. 6B, in other embodiments, the medical device 100 may include a first actuating element 120a and a second actuating element 120b coupled to the exterior surface of the wall 130 of the elongated tube 110. As shown in the figure, the first actuating element 120a and the second actuating element 120b are both located on a same side of the elongated tube 110. This configuration allows the actuating elements 120a, 120b to bend different segments of the elongated tube 110 towards the same side of the elongated tube 110 (i.e., in a same bending plane).

Figure 6C:
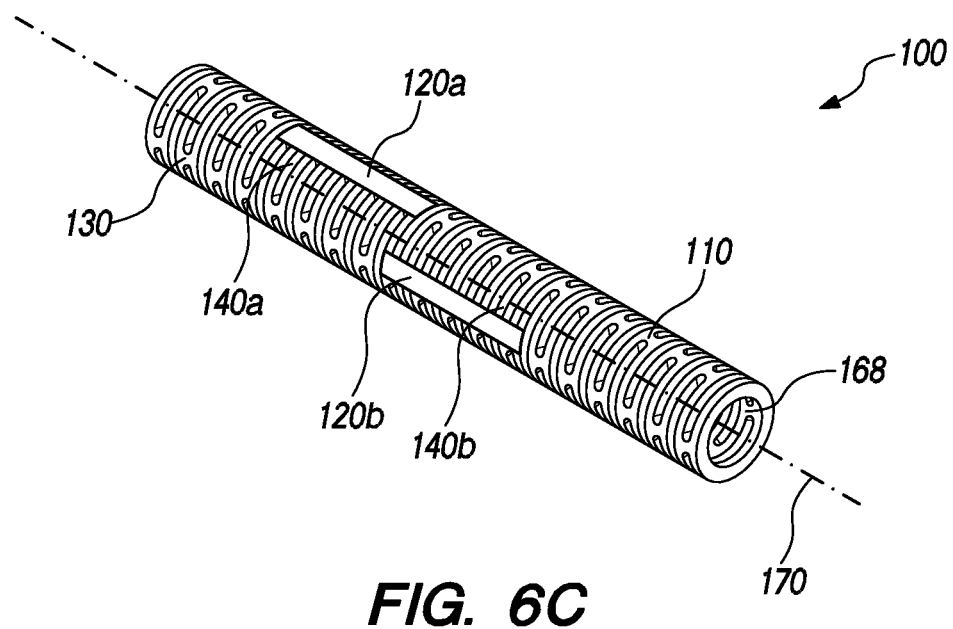
FIG. 6C illustrates a medical device having a tube and a plurality of actuating elements for bending the tube in accordance with other embodiments.

In other embodiments, the first actuating element 120a and the second actuating element 120b may be located on different respective sides of the elongated tube 110 (FIG. 6C). This configuration allows the actuating elements 120a, 120b to bend the elongated tube 110 in different bending planes. For example, the first actuating element 120a may be configured to cause the elongated tube 110 to bend in a first direction in a first bending plane, and the second actuating element 120b may be configured to cause the elongated tube 110 to bend in a second direction (in a second bending plane) that is different from the first direction.

Figure 6D:
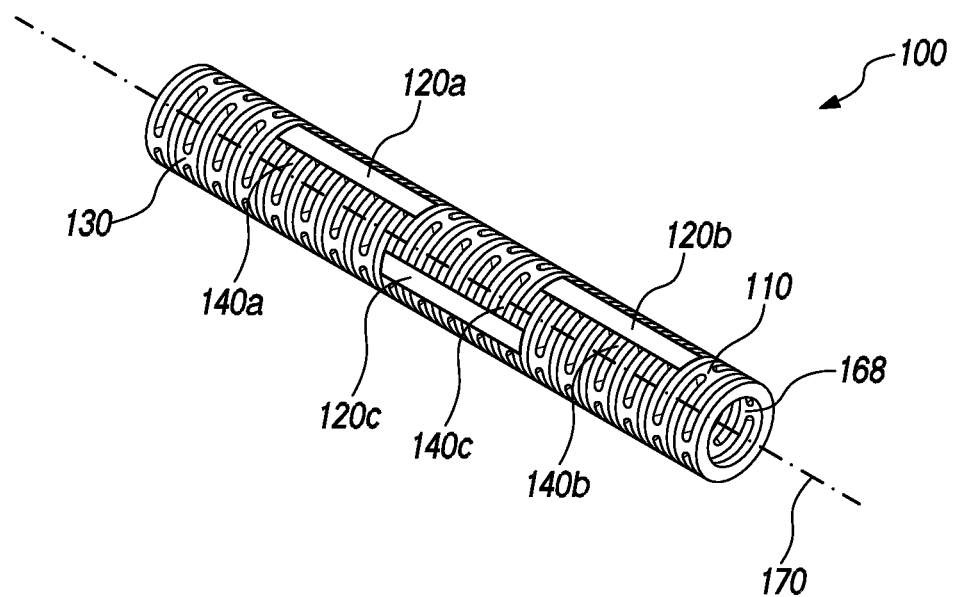
FIG. 6D illustrates a medical device having a tube and a plurality of actuating elements for bending the tube in accordance with other embodiments.

In further embodiments, the medical device 100 may include more than two actuating elements 120. FIG. 6D illustrates a medical device 100 having an elongated tube 110 and a plurality of actuating elements 120 for bending the elongated tube 110 in accordance with other embodiments. The medical device 100 is the same as that shown in FIG. 6B, except that the medical device 100 further includes a third actuating element 120c coupled to an exterior surface of the wall 130 of the elongated tube 110. The third actuating element 120c has the same configuration as that of the first actuating element 120a. As shown in the figure, the first and second actuating elements 120a, 120b are located at the same circumferential position with respect to the longitudinal axis 170 of the elongated tube 110, and the third actuating element 120c is located at a different circumferential position from that of the first and second actuating elements 120a, 120b with respect to the longitudinal axis 170. Such configuration allows the first and second actuating elements 120a, 120b to bend the elongated tube 110 in a first bending plane, and also allows the third actuating element 120c to bend the elongated tube 110 in a second bending plane that is different from the first bending plane. The first and second actuating elements 120a, 120b allow bending of different segments along the length of the elongated tube 110. In further embodiments, the medical device 100 may optionally include a fourth opening and a fourth actuating element located in the fourth opening. The third and fourth actuating elements may be located at the same circumferential position with respect to the longitudinal axis 170 of the elongated tube 110. This allows the third and the fourth actuating elements to bend different segments of the elongated tube 110 in the same bending plane.

In other embodiments, instead of coupling the actuating element(s) 120 to the exterior surface of the elongated tube 110 like those shown in FIGS. 6A-6D, the actuating element(s) 120 may be coupled to an interior surface of the elongated tube 110. For example, one or more actuating elements 120 may be coupled to an interior surface of the wall 130 of the elongated tube 110.

Also, in any of the embodiments of FIGS. 6A-6D, the actuating elements 120 may have any lengths, which may be different from the examples illustrated. For example, in some embodiments, an actuating element 120 may be made relatively long to achieve a relatively large overall bending movement and bent profile.

It should be noted that in the embodiments of FIGS. 5-6, the medical device 100 is not limited to having one opening 140 (e.g., slot) per longitudinal plane, and that in other embodiments, the medical device 100 may have two or more openings 140 (e.g., two or more slots) per longitudinal plane. The openings 140 (e.g., slots) need not be equal in size in a given longitudinal plane, and/or in other parallel planes. In some embodiments, the openings 140 may be slots collectively forming a helix or other pattern around the tube 110, with the actuating element(s) 120 following the same helix, so that the actuating element(s) 120 form a helix or other pattern.

Figure 7A:
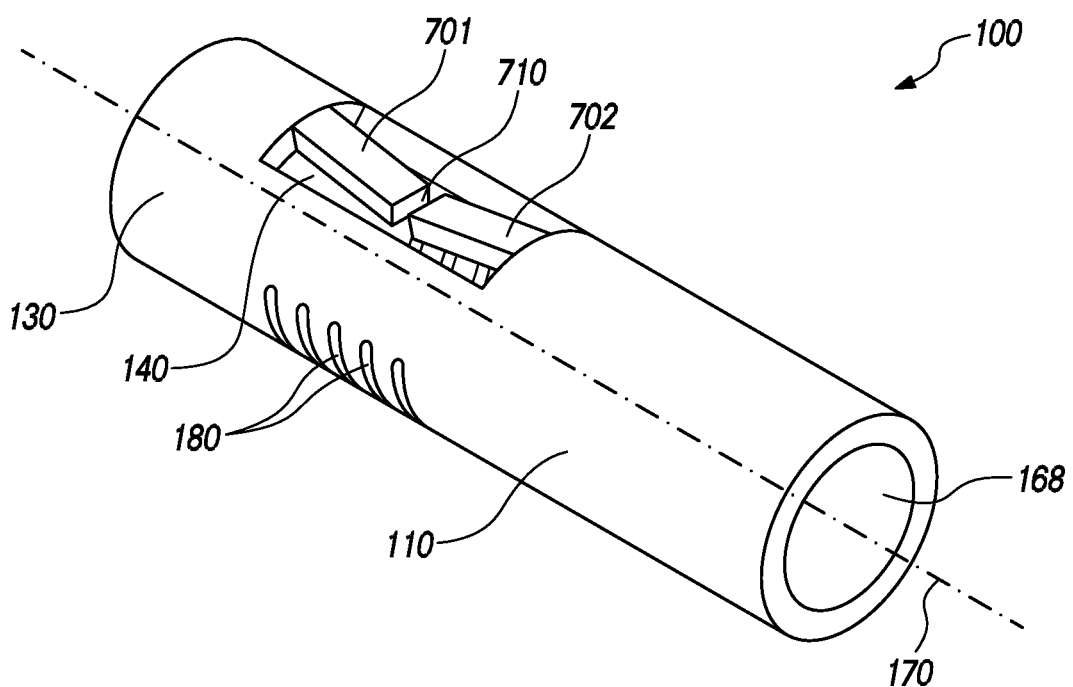
FIG. 7A illustrates a medical device having a tube and an actuating element for bending the tube in accordance with other embodiments.
Figure 7B:
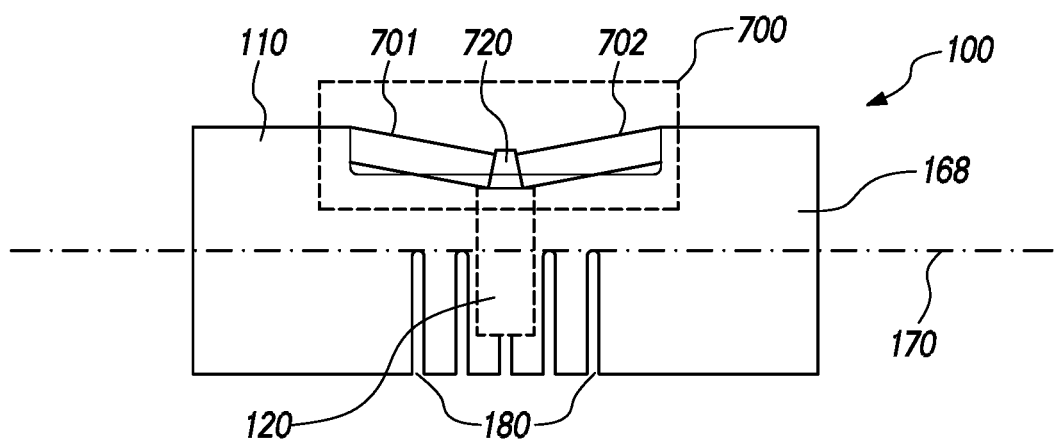
FIG. 7B illustrates a side view of the medical device of FIG. 7A.

Also, it should be noted that the medical device 100 is not limited to the examples described, and that the medical device 100 may have other configurations in other embodiments. For example, in other embodiments, the medical device 100 may include one or more actuating elements 120 located in the lumen 168 of the elongated tube 100. FIGS. 7A-7B illustrate another medical device 100 having a bendable elongated tube 110 in accordance with other embodiments. The elongated tube 110 has a wall 130 with an opening 140. The elongated tube 110 also includes a structural member 700 (FIG. 7B) located in the opening 140. In the illustrated embodiments, the structural member 700 is coupled between opposite sides of the opening 140. The structural member 700 has a length that is longer than a dimension of the opening 140. As shown in FIG. 7B, the medical device 100 further includes an actuating element 120 disposed in the lumen 168 of the elongated tube 110. The actuating element 120 is configured to apply a force towards the structural member 700. In the illustrated embodiments, the actuating element 120 is configured to expand in order to apply the force in a direction that is perpendicular to the longitudinal axis 170 of the elongated tube 110. In particular, expansion of the actuating element 120 pushes an intermediate or central part of the structural member 700 into the opening 140 in a direction that is away from the lumen 168 of the elongated tube 110. This results in opposite ends of the opening 140 being pushed away from each other by the structural member 700 (because the structural member 700 is longer than the dimension of the opening 140), causing the elongated tube 110 to bend in a direction that is opposite the pushing force exerted by the actuating element 120.

Different techniques may be employed to make the structural member 700 so that it is longer than the dimension of the opening 140. As shown in FIG. 7A, in the illustrated embodiments, parts 701, 702 of the structural member 700 may be created by cutting the elongated tube 110 (e.g., using laser cutting). As shown in the figure, the parts 701, 702 are created so that they are not connected together, and there is a spacing 710 between the parts 701, 702. Then the parts 701, 702 are bent inward towards the lumen 168 so that the parts 701, 702 form respective non-zero angles with respect to the longitudinal axis 170 of the elongated tube 110 (as shown in FIGS. 7A-7B). In some embodiments, the bending of the parts 701, 702 may involve plastically deforming or heat setting the parts 701, 702. Next, a bridging element 720 may be placed between the parts 701, 702 to connect the parts 701, 702 together. The bridging element 720 may be any rigid element. The bridging element 720 may be secured to the parts 701, 702 using glue, adhesive, welding, or any of other techniques known in the art. The parts 701, 702, and the bridging element 720 together form the structural member 700. In other embodiments, the opening 140 may be made without the parts 701, 702. In such cases, after the opening 140 is made, the structural member 700 may be placed in the opening 140 with opposite ends secured to opposite sides of the opening 140. In such embodiments, the structural member 700 may be an integral component, such as a strip of material having a bent configuration. In other embodiments, the bridging element 720 could be a single integral element bridging from one end of the opening to the opposite end, wherein the bridging element 720 may be plastically deformed (stretched) inward into the lumen 168 of the elongated tube 110.

In other embodiments, the structural member 700 may have a length that is the same as the dimension of the opening 140. In such cases, the actuating element 120 may be configured to contract in order to pull at least a part of the structural member 700 out of the opening 140 in a direction that is towards the lumen 168 of the elongated tube 110. This results in opposite ends of the opening 140 being pulled towards each other, causing the elongated tube 110 to bend in a direction that is opposite the pulling force exerted by the actuating element 120.

In some embodiments, the actuating element 120 may be in a form of a ring with a central opening. Such configuration allows a substance or an object in the lumen 168 of the elongated tube 110 to pass therethrough. In other embodiments, the actuating element 120 may have other shapes. For example, in other embodiments, the actuating element 120 may have a block-like configuration that does not completely occlude the lumen 168. In further embodiments, the actuating element 120 may completely occlude the lumen 168. The actuating element 120 may be implemented using any of the techniques described with reference to FIG. 1.

In the illustrated embodiments, the parts 701, 702 have respective major lengths that are oriented in a direction parallel to the longitudinal axis 170 of the elongated tube 110. In other embodiments, the parts 701, 702 may extend circumferentially rather than longitudinally as shown. In still further embodiments, the medical device 100 of FIG. 7A may optionally include linkages, like the linkages 60a, 62a, 60b, 62b described with reference to FIG. 1 to amplify deflection. In such cases, the linkages may be coupled to the structural member 700 for receiving forces applied by the structural member 700 due to actuation of the actuating element 120.

As shown in FIG. 7A, the medical device 100 includes only one actuating element 120. In other embodiments, the medical device 100 may include a plurality of actuating elements 120 disposed at different longitudinal positions with respect to the longitudinal axis 170 of the elongated tube 110. For example, in other embodiments, the medical device 100 may include a first actuating element 120 and a second actuating element 120 located in respective openings 140 of the wall 130 of the elongated tube 110. The first actuating element 120 and the actuating elements 120 may be configured to push and/or pull respective structural members 700 located on a same side of the elongated tube 110. This configuration allows the actuating elements 120 to bend different segments of the elongated tube 110 towards the same side of the elongated tube 110 (i.e., in a same bending plane).

In other embodiments, the first actuating element 120 and the second actuating element 120 may be configured to push and/or pull respective structural members 700 located on different respective sides of the elongated tube 110. This configuration allows the actuating elements 120 to bend the elongated tube 110 in different bending planes. For example, a first actuating element 120 may be configured to cause the elongated tube 110 to bend in a first direction in a first bending plane, and the second actuating element 120 may be configured to cause the elongated tube to bend in a second direction (in a second bending plane) that is different from the first direction.

In further embodiments, the medical device 100 may include more than two actuating elements 120 configured to push and/or pull respective structural members 700 disposed at different segments of the elongated tube 110.

In any of the embodiments described herein, the actuating element 120 may be actuatable to provide different degrees of bending. For example, in the case in which the actuating element 120 is actuatable in response to energy, the amount of energy may be variable to cause the actuating element 120 to provide different degrees of bending for the elongated tube 110. In other embodiments, the actuating element 120 may be bi-modal in that it can only be turned on or off. In such cases, the actuating element 120 does not provide different degrees of bending, and provides a pre-determined degree of bending. Similarly, if the medical device 100 includes multiple of such actuating elements 120 (where the degree of expansion/contraction of each actuating element 120 is bi-modal (on/off), rather than incrementally controllable), different number and/or combination of the actuating elements 120 may be selectively actuated to achieve different degrees of bending for the elongated tube 110.

In any of the embodiments described herein, the elongated tube 110 may be a part of a catheter, a guidewire, or an implant. Accordingly, any of the actuating element(s) 120 described herein may be implemented as component(s) of a catheter for bending the catheter, component(s) of a guidewire for bending the guidewire, or component(s) of an implant for bending the implant.

Figure 8:
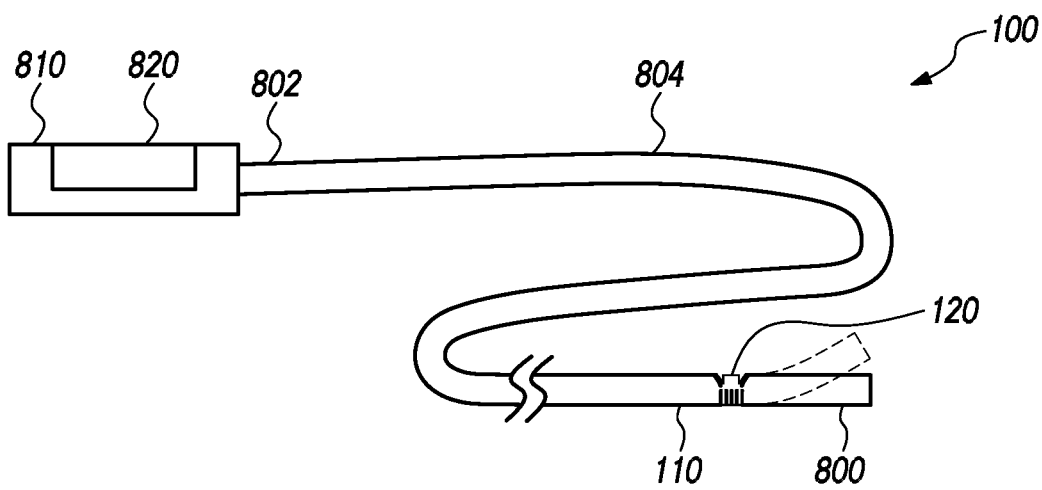
FIG. 8 illustrates a catheter in accordance with some embodiments.

FIG. 8 illustrates the elongated tube 110 being a part of a catheter in accordance with some embodiments. The medical device 100, which is the catheter in the illustrated embodiments, includes a catheter body 804 having a distal end 800 and a proximal end 802. The medical device 100 also includes a handle 810 coupled to the proximal end 802 of the catheter body 804, and a user interface 820 configured for allowing a user to control a bending of the catheter body 804. The user interface 820 is illustrated as being implemented at the handle 810, but in other embodiments, the user interface 820 may be implemented as another device that is separate from the handle 810. For example, in other embodiments, the user interface 820 may be a computer or any electronic device (e.g., cell phone, tablet, etc.) that is capable of generating electrical signals and/or radiofrequency signals. As shown in the figure, the catheter body 804 includes an actuating element 120, which may be any of the embodiments of the actuating element 120 described herein. The actuating element 120 is actuatable in response to electrical signals or radiofrequency signals provided by the user interface 820, to thereby bend the catheter body 804. In other embodiments, the catheter body 804 may include a plurality of actuating elements 120. The user interface 820 may include one or more controls for allowing the user to activate the actuating element(s) 120 at the catheter body 804 to thereby bend the catheter body 804. In some embodiments, the one or more controls may be one or more physical button(s), knob(s), switch(es), etc. In other embodiments, the one or more controls may be a touch screen with graphical elements configured to allow the user to activate the actuating element(s) 120 at the catheter body 804.

During use of the catheter, the catheter body 804 is inserted into a patient's body. As the catheter body 804 is being advanced inside the patient, the user interface 820 may be operated by the user to actuate the actuating element(s) 120 to cause the distal segment of the catheter body 804 to bend in a desired manner. The bending of the catheter body 804 allows the distal end 800 of the catheter body 804 to be steered through different curvatures along a passage way (e.g., blood vessel) inside the patient. In some embodiments, the catheter body 804 may be rotated about its longitudinal axis to allow the bending to occur at different bending planes. Also, in some embodiments, a degree (e.g., curvature, angle, etc.) of bending of the catheter body 804 may be adjusted by varying a magnitude of the energy (e.g., current or voltage) or displacement provided by the user interface 820. In some instances, the bending of the catheter body may serve to position the catheter tip in a desirable location or orientation, or to hold the catheter in a particular orientation or location within the patient. Additionally, the bending or straightening of the catheter body may serve to modify the shape of the passage (e.g., blood vessels) in which the catheter body is deployed.

After the distal end 800 of the catheter body 804 has been desirably positioned inside the patient, the catheter body 804 may then be utilized in a medical procedure to diagnose and/or treat the patient. For examples, the catheter body 804 may be used to deliver a substance (e.g., drug, medicine, contrast, saline, etc.), deploy a device (e.g., implant, tissue dissector, imaging scope, treatment energy source, etc.), or perform other functions in different embodiments.

Figure 9:
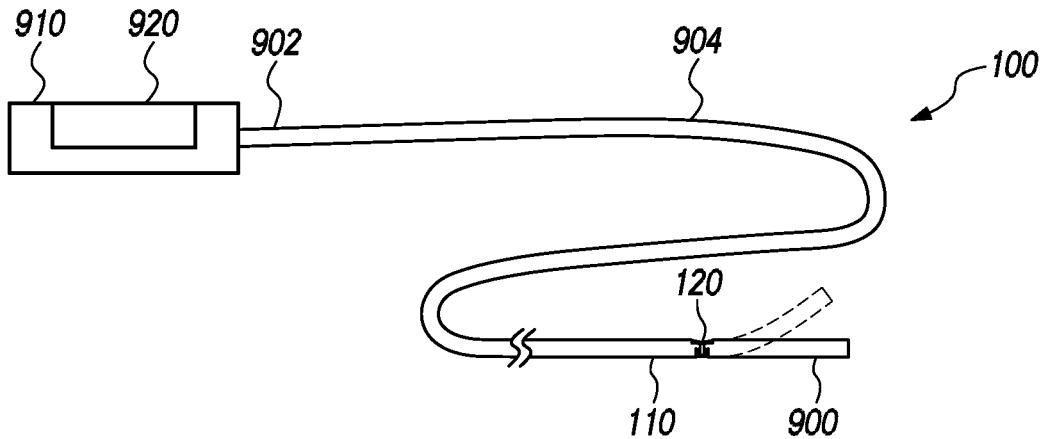
FIG. 9 illustrates a guidewire in accordance with some embodiments.

FIG. 9 illustrates the elongated tube 110 being a part of a guidewire in accordance with some embodiments. The medical device 100, which is the guidewire in the illustrated embodiments, includes a guidewire body 904 having a distal end 900 and a proximal end 902. The medical device 100 also includes a handle 910 coupled to the proximal end 902 of the guidewire body 904, and a user interface 920 configured for allowing a user to control a bending of the guidewire body 904. The user interface 920 is illustrated as being implemented at the handle 910, but in other embodiments, the user interface 920 may be implemented as another device that is separate from the handle 910. For example, in other embodiments, the user interface 920 may be a computer or any electronic device (e.g., cell phone, tablet, etc.) that is capable of generating electrical signals and/or radiofrequency signals. As shown in the figure, the guidewire body 904 includes an actuating element 120, which may be any of the embodiments of the actuating element 120 described herein. The actuating element 120 is actuatable in response to electrical signals or radiofrequency signals provided by the user interface 920, to thereby bend the guidewire body 904. In other embodiments, the guidewire body 904 may include a plurality of actuating elements 120. The user interface 820 may include one or more controls for allowing the user to activate the actuating element(s) 120 at the guidewire body 904 to thereby bend the guidewire body 904. In some embodiments, the one or more controls may be one or more physical button(s), knob(s), switch(es), etc. In other embodiments, the one or more controls may be a touch screen with graphical elements configured to allow the user to activate the actuating element(s) 120 at the guidewire body 904.

During use of the guidewire, the guidewire body 904 is inserted into a patient's body. As the guidewire body 904 is being advanced inside the patient, the user interface 920 may be operated by the user to actuate the actuating element(s) 120 to cause the distal segment of the guidewire body 904 to bend in a desired manner. The bending of the guidewire body 904 allows the distal end 900 of the guidewire body 904 to be steered through different curvatures along a passage way (e.g., blood vessel) inside the patient. In some embodiments, the guidewire body 904 may be rotated about its longitudinal axis to allow the bending to occur at different bending planes. Also, in some embodiments, a degree (e.g., curvature, angle, etc.) of bending of the guidewire body 904 may be adjusted by varying a magnitude of the energy (e.g., current or voltage) or displacement provided by the user interface 820. In some instances, the bending of the guidewire body may serve to position the guidewire tip in a desirable location or orientation, or to hold the guidewire in a particular orientation or location within the patient. Additionally, the bending or straightening of the guidewire body may serve to modify the shape of the passage (e.g., blood vessels) in which the guidewire body is deployed.

After the distal end 900 of the guidewire body 904 has been desirably positioned inside the patient, the guidewire body 904 may then be utilized in a medical procedure. For examples, another device (which may be a diagnostic device or a treatment device) inserted over the guidewire body 904 may be advanced inside the patient, using the guidewire body 904 as a guide to reach a target location inside the patient.

Figure 10:
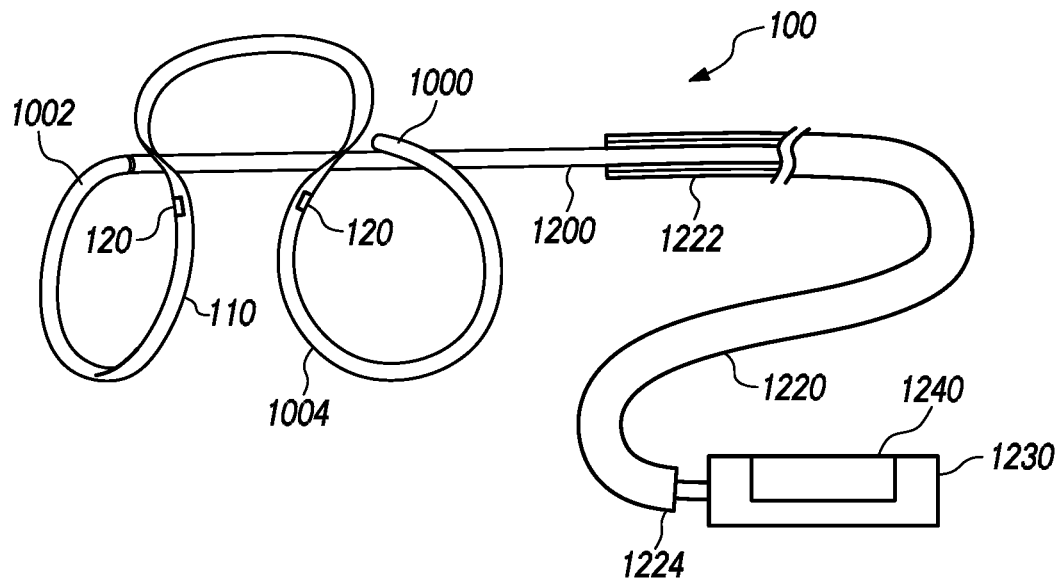
FIG. 10 illustrates an implant in accordance with some embodiments.

FIG. 10 illustrates the elongated tube 110 being a part of an implant in accordance with some embodiments. The medical device 100, which is the implant in the illustrated embodiments, includes a distal end 1000, a proximal end 1002, and an implant body 1004 extending between the distal end 1000 and the proximal end 1002. In the illustrated example, the implant 100 is a vaso-occlusive implant configured to be delivered into a blood vessel to reach an aneurysm for treating the aneurysm. In other examples, the implant 100 may be other types of implant such as a stent. As shown in the figure, the proximal end 1002 of the implant 100 is detachably coupled to a delivery wire 1200. The implant 100 with the delivery wire 1200 may be contained in a delivery tube 1220 during use. The delivery tube 1220 includes a distal end 1222 and a proximal end 1224. The proximal end 1224 of the delivery tube 1220 is attached to a handle 1230, which includes a user interface 1240. The user interface 1240 may be implemented to have the same features as those described with reference to FIGS. 8 and 9. The user interface 1240 may be configured for allowing a user to control a bending of the implant 100. The user interface 1240 is illustrated as being implemented at the handle 1230, but in other embodiments, the user interface 1240 may be implemented as another device that is separate from the handle 1230. For example, in other embodiments, the user interface 1240 may be a computer or any electronic device (e.g., cell phone, tablet, etc.) that is capable of generating electrical signals and/or radiofrequency signals. As shown in the figure, the implant 100 includes actuating elements 120, each of which may be any of the embodiments of the actuating element 120 described herein. The actuating elements 120 are actuatable in response to electrical signals or radiofrequency signal provided by the user interface 1240, to thereby bend the implant 100.

During use, the implant 100 and the delivery wire 1200 are contained in the delivery tube 1220. The delivery tube 1220 is inserted into a blood vessel of a patient and is advanced to reach a target site, such as an aneurysm. If the delivery tube 1220 has steering capability, such as any of the bending techniques described herein, or if the delivery tube 1220 has steering wires, the delivery tube 1220 may be bent to navigate through the blood vessel inside the patient. After the delivery tube 1220 has reached an aneurysm, the delivery wire 1200 may be advanced relative to the delivery tube 1220 to deploy the implant 100 out of the delivery tube 1220, and into the aneurysm. As the implant 100 is being deployed into the aneurysm, or after the implant 100 has been deployed into the aneurysm, the user interface 1240 may be operated by the user to actuate the actuating element(s) 120 to cause certain parts of the implant 100 to bend in a desired manner. The bending of the implant 100 allows the implant 100 to have a certain geometry (e.g., size and/or shape) that fits inside the aneurysm in a desired manner. Also, in some embodiments, a degree (e.g., curvature, angle, etc.) of bending of the implant 100 may be adjusted by varying a magnitude of the energy (e.g., current, voltage, or another type of energy) provided by the user interface 1240. In addition, in some embodiments, the implant 100 may have a pre-bent configuration that includes a series of loops. In such cases, the implant 100 may have an actuating element 120 disposed between adjacent loops, and/or may have an actuating element 120 disposed along a segment of a loop. The pre-bent configuration of the implant 100 provides a certain relaxed three-dimensional configuration for the implant 100, and the actuating elements 120 may be selectively actuated to adjust such relaxed three-dimensional configuration. Alternately, the position of specific loops of the implant could be adjusted during deployment of the implant, so that the arrangement of the implant loops is optimized for occlusion of the aneurysm. In another embodiment, the pre-bent implant could be delivered in a relatively straight configuration, then allowed to tighten up its structure by resuming its pre-bent shape upon discontinuation of the actuating signal. This could improve packing density and interlocking with other occlusive devices inside the aneurysm, and thus improved occlusion. In other embodiments, the implant 100 may not have any pre-bent configuration. Instead, the implant 100 may have a relatively straight relaxed profile. In such cases, the implant 100 may have a plurality of actuating elements 120 disposed along a majority of its length. As the implant 100 is being delivered into the aneurysm, the user-interface 1240 may be operated to selectively bend certain segments of the implant 100 to form a three-dimensional configuration in situ. Upon discontinuation of the actuating signal, the implant will attempt to resume its relatively straight relaxed profile, but may be constrained from fully doing so by a restraining membrane or structure, such as an intrasaccular device.

In some embodiments, the implant may have one or more actuating elements that incorporate plastic deformation, so that the implant is bent during or after deployment, and retains the bent configuration after removal of the actuating signal. One application of such a configuration is for ensuring that the proximal end of the implant, e.g., a vaso-occlusive coil, stays inside the aneurysm in which it is deployed, rather than protruding into a parent vessel.

In some embodiments, one technique of bending selected portion(s) of the implant would be to employ a shape-memory element as the actuator. The shape-memory element may be heated resistively through the application of electrical current, before detachment from the delivery wire. Alternatively, the shape-memory element may be heated inductively by radiofrequency energy generated within the delivery catheter or by a separate device (e.g., guidewire), by contact with or proximity to an elevated-temperature surface, or by delivery of a fluid at elevated temperature. This approach may allow the implant to have multiple actuator elements, but give the physician the option of actuating some, none, or all of them depending on the conditions of the specific implant deployment.

In any of the embodiments described herein, the elongated tube 110 may be made of any material, such a polymer, a metal, an alloy, etc. In some embodiments, the elongated tube 110 may be a hypotube. Also, in any of the embodiments described herein, the medical device 100 may further include an outer tubular layer disposed over the elongated tube 110. The outer tubular layer may be attached directly or indirectly to an outer surface of the wall 130 of the elongated tube 110. The outer tubular layer may function to contain the actuating element 120 and/or to achieve a smooth surface over the region where the opening 140 is located. Also, in any of the embodiments described herein the medical device 100 may include an inner tubular layer disposed in the lumen 168 of the elongated tube 110. The inner tubular layer may be attached directly or indirectly to an inner surface of the wall 130 of the elongated tube 110. The inner tubular layer may function to cover the opening 140. The outer and inner tubular layers may be made from a material that is softer than the material of the elongated tube 110 so that they will not interfere with a bending of the elongated tube 110.

It should be noted that the medical device 100 described herein may have other features and configurations in other embodiments. For example, in other embodiments, a geometry (e.g., size, orientation, shape, etc.) of the opening 140 and/or a configuration of the actuating element 120 may be tailored to achieve a certain deflection of the elongated tube 110. In further embodiments, if the medical device 100 includes linkages (such as the linkages 160, 162 described with referent to the embodiments of FIG. 1), the linkages may be tailored to achieve a certain deflection of the elongated tube 110. Also, in other embodiments, a direction of pushing or pulling force applied by the actuating element 120 may be selectively configured to be in any direction that is different from the examples described herein. Furthermore, in other embodiments, the geometry of the opening 140, the configuration of the actuating element 120, the linkages, or any combination of the foregoing, may be selectively tailored to achieve a certain force amplification or amplitude amplification. In a force amplification, a certain force applied by the actuating element 120 will result in certain amount of bending force. In an amplitude amplification, a certain amplitude movement of the actuating element 120 (due to its change in size) will result in certain amount of displacement at a tip of the elongated tube 110.

In some embodiments, the geometry of the opening 140, the configuration of the actuating element 120, the linkages, the material properties of the elongated tube 110, or any combination of the foregoing, may be selectively tailored to achieve elastic deformation of the element 120 and/or the elongated tube 110 (and thus reversible bending of the elongated tube 110), so that when the energy source is turned off, the elongated tube 110 resumes its original shape. In other embodiments, the geometry of the opening 140, the configuration of the actuating element 120, the linkages, the material properties of the elongated tube 110, or any combination of the foregoing, may be selectively tailored to achieve plastic deformation of the element 120 and/or the elongated tube 110 (and thus irreversible bending of the elongated tube 110), so that when the energy source is turned off, the elongated tube 110 does not resume its original shape. In further embodiments, the medical device 100 may incorporate both elastic and plastic deformation in differing degrees and proportions. For example, in some embodiments, the geometry of the opening 140, the configuration of the actuating element 120, the material properties of the elongated tube 110, or any combination of the foregoing, may be selectively tailored to achieve both elastic and plastic deformation in differing degrees and proportions at one or more locations in the medical device 100.

Techniques for bending the elongated tube 110 described herein are advantageous because they allow selective bending of the elongated tube 110 while the elongated tube 110 is disposed inside the patient without using steering wires. Unlike a steering wire, which extends all the way from the distal end of a medical device to a proximal end, the actuating element 120 described herein does not extend to the proximal end of the medical device 100. Instead, the extent of the actuating element 120 stay localized within certain zone at a segment of the elongated tube 110. As illustrated in the above embodiments, at least a part of the actuating element 120 and the corresponding opening 140 of the wall 130 are located at a same longitudinal position with respect to a longitudinal axis 170 of the elongated tube 110. Because no steering wires are needed, the elongated tube 110 and the medical device 100 comprising such elongated tube 110 may be made smaller. Smaller medical device 100 is desirable because it can navigate and can reach smaller space inside the patient. For example, if the medical device 100 is a catheter, a guidewire, or an implant, such medical device 100 may reach target areas that are at narrower blood vessels, such as those in patients' brains. Also, because the bending of the medical device 100 does not require any steering wires (such as pull wires), there is minimal or zero net shortening of the medical device 100 in its deflected or bent state, and there is no tendency of straightening a proximal portion of the medical device 100 (which may occur due to tensioning exerted in a pull wire). Furthermore, because there are no pull wires in the medical device 100, there is no risk of inadvertently moving the medical device 100 by a user while trying to actuate the deflection of the medical device 100. In addition, because the medical device 100 does not require any steering wires, there are no mechanical issues associated with use of such steering wires, such as detachment of steering wire from the catheter body, steering wire getting stuck due to frictional contact with the catheter body, etc.

Also, the bending techniques described herein are advantageous because they allow creation of sharp bend of the medical device 100. In the case in which the medical device 100 is a catheter or a guidewire, this feature allows the medical device 100 to navigate through sharp bend in blood vessels of a patient.

In addition, for the cases in which the medical device 100 is a guidewire or an implant (such as a vaso-occlusive device), techniques for bending the elongated tube 110 described herein are also advantageous for these applications. This is because the lack of steering wires allows the guidewire or the implant to be made smaller. Also, the technique for bending the guidewire or the implant described herein allows the guidewire or the implant to be selective bent in one or more directions while the guidewire or the implant is inside the patient. In addition, because the guidewire or the implant may be selectively bent in one or more directions even after they are delivered inside the patient, the guidewire or the implant may have a relatively straight profile that corresponds with a profile of a delivery tube housing such guidewire or implant. This allows the guidewire or the implant to be advanced inside the delivery tube with minimal friction.

The following items are exemplary features of embodiments described herein. Each item may be an embodiment itself or may be a part of an embodiment. One or more items described below may be combined with other item(s) in an embodiment.

Item 1: A medical device includes: an elongated tube having a wall, wherein the wall of the elongated tube comprises a first opening; and a first actuating element located in the first opening of the wall of the elongated tube; wherein the first actuating element in the first opening of the wall is actuatable to induce stress and/or displacement at the wall of the elongated tube to cause the elongated tube to bend.

Item 2: A size of the first actuating element is variable to induce the stress and/or the displacement at the wall of the elongated tube to cause the elongated tube to bend.

Item 3: The size of the actuating element is variable in a direction that is parallel to a longitudinal axis of the elongated tube.

Item 4: The size of the actuating element is variable in a direction that is perpendicular to a longitudinal axis of the elongated tube.

Item 5: The first actuating element is at a first side of the elongated tube, and the elongated tube comprises one or more slots, or other structural feature(s), at a second side of the elongated tube, the second side being opposite from the first side.

Item 6: The first actuating element is configured to expand, to contract, or to both expand and to contract.

Item 7: The first actuating element is configured to expand within the first opening of the wall to cause the elongated tube to bend in a first direction, and wherein the first actuating element is configured to contract within the opening of the wall to cause the elongated tube to bend in a second direction that is opposite from the first direction.

Item 8: The wall of the elongated tube comprises a first linkage and a second linkage coupled with respective opposite sides of the first actuating element.

Item 9: The first actuating element is configured to apply opposite forces towards the first and second linkages to induce the stress and/or the displacement at the wall of the elongated tube.

Item 10: The first linkage comprises a first part of the wall, and the second linkage comprises a second part of the wall, the first and second parts of the wall formed by laser-cutting, etching, or removing material from, the elongated tube.

Item 11: The first actuating element comprises a piezo element, a balloon, an electroactive polymer, or a shape-memory element.

Item 12: The first actuating element is actuatable in response to electrical energy, radiofrequency energy, thermal energy, delivery of fluid, or pressure.

Item 13: The wall of the elongated tube comprises a second opening, and wherein the medical device further comprises a second actuating element located in the second opening of the wall of the elongated tube.

Item 14: The first actuating element and the second actuating element are located on a same side of the elongated tube.

Item 15: The first actuating element and the second actuating element are located on different respective sides of the elongated tube.

Item 16: The first actuating element is configured to cause the elongated tube to bend in a first direction, and the second actuating element is configured to cause the elongated tube to bend in a second direction that is different from the first direction.

Item 17: The elongated tube is a part of a catheter.

Item 18: The elongated tube is a part of a guidewire.

Item 19: The elongated tube is a part of an implant.

Item 20: The implant is configured to deform plastically.

Item 21: The first actuating element and/or the elongated tube is configured to deform elastically.

Item 22: The first actuating element and/or the elongated tube is configured to deform plastically.

Item 23: A medical device includes: an elongated tube having a wall defining a lumen for the elongated tube, wherein the wall of the elongated tube comprises a first opening; and a first actuating element coupled directly or indirectly to the wall of the elongated tube; wherein at least a part of the first actuating element and the first opening of the wall are located at a same longitudinal position with respect to a longitudinal axis of the elongated tube; and wherein the first actuating element is configured to change size to induce stress and/or displacement at the wall of the elongated tube to cause the elongated tube to bend.

Item 24: The first actuating element is configured to alter a cross-sectional dimension of the first opening to induce the stress and/or the displacement at the wall of the elongated tube.

Item 25: The first actuating element is actuatable, and is located in the first opening of the wall of the elongated tube.

Item 26: The wall of the elongated tube comprises a first linkage and a second linkage coupled with respective opposite sides of the first actuating element.

Item 27: The first actuating element is configured to apply opposite forces towards the first and second linkages to induce the stress and/or the displacement at the wall of the elongated tube.

Item 28: The wall of the elongated tube comprises a second opening, and wherein the medical device further comprises a second actuating element located in the second opening of the wall of the elongated tube.

Item 29: The first actuating element is configured to cause the elongated tube to bend in a first direction, and the second actuating element is configured to cause the elongated tube to bend in a second direction that is the same as, or different from, the first direction.

Item 30: The first actuating element extends across the first opening of the wall of the elongated tube.

Item 31: The first actuating element is coupled to an exterior surface of the elongated tube.

Item 32: The first actuating element is coupled to an interior surface of the elongated tube.

Item 33: The wall of the elongated tube further comprises a second opening, and wherein the first actuating element also extends across the second opening of the wall of the elongated tube.

Item 34: The elongated tube comprises a distal end and a proximal end, and wherein the first actuating element is located between the distal end and the proximal end of the elongated tube.

Item 35: The medical device further includes a structural member coupled between opposite sides of the first opening, wherein the first actuating element is located in the lumen of the elongated tube, and is configured to apply a force towards the structural member.

Item 36: The structural member has a length that is longer than a dimension of the opening.

Item 37: The first actuating element is configured to apply the force in a direction that is perpendicular to the longitudinal axis of the elongated tube.

Item 38: The first actuating element is at a first side of the elongated tube, and the elongated tube comprises one or more slots, or other structural feature(s), at a second side of the elongated tube, the second side being opposite from the first side.

Item 39: The first actuating element is configured to expand, to contract, or to both expand and to contract.

Item 40: The first actuating element comprises a piezo element, a balloon, an electroactive polymer, or a shape-memory element.

Item 41: The first actuating element is actuatable in response to electrical energy, radiofrequency energy, thermal energy, delivery of fluid, or pressure.

Item 42: The elongated tube is a part of a catheter, a part of a guidewire, or a part of an implant.

Item 43: The implant is configured to deform plastically.

Item 44: The first actuating element and/or the elongated tube is configured to deform elastically.

Item 45: The first actuating element and/or the elongated tube is configured to deform plastically.

Although particular embodiments have been shown and described, it will be understood that it is not intended to limit the claimed inventions to the preferred embodiments, and it will be obvious to those skilled in the art that various changes and modifications may be made without department from the scope of the claimed inventions. The specification and drawings are, accordingly, to be regarded in an illustrative rather than restrictive sense. The claimed inventions are intended to cover alternatives, modifications, and equivalents.

What is claimed is:

1. A medical device, comprising:
   an elongated tube having a wall, wherein the wall of the elongated tube comprises a first opening;
   a first actuating element located in the first opening of the wall of the elongated tube, wherein the first actuating element in the first opening of the wall is actuatable to induce stress and/or displacement at the wall of the elongated tube to cause the elongated tube to bend; and
   a first linkage and a second linkage in the first opening of the wall of the elongated tube, wherein the first linkage and the second linkage are coupled with the first actuating element.

2. The medical device of claim 1, wherein a size of the first actuating element is variable to induce the stress and/or the displacement at the wall of the elongated tube to cause the elongated tube to bend.

3. The medical device of claim 2, wherein the size of the actuating element is variable in a direction that is parallel to a longitudinal axis of the elongated tube.

4. The medical device of claim 2, wherein the size of the actuating element is variable in a direction that is perpendicular to a longitudinal axis of the elongated tube.

5. The medical device of claim 1, wherein the first actuating element is at a first side of the elongated tube, and the elongated tube comprises one or more slots, or other structural feature(s), at a second side of the elongated tube, the second side being opposite from the first side.

6. The medical device of claim 1, wherein the first actuating element is configured to expand, to contract, or both to expand and contract.

7. The medical device of claim 6, wherein the first actuating element is configured to expand within the first opening of the wall to cause the elongated tube to bend in a first direction, and wherein the first actuating element is configured to contract within the opening of the wall to cause the elongated tube to bend in a second direction that is opposite from the first direction.

8. The medical device of claim 1, wherein the wall of the elongated tube comprises the first linkage and the second linkage coupled with respective opposite sides of the first actuating element, wherein the first linkage includes at least a first structural member and a second structural member.

9. The medical device of claim 8, wherein the first actuating element is configured to apply opposite forces towards the first and second linkages to induce the stress and/or the displacement at the wall of the elongated tube.

10. The medical device of claim 8, wherein the first linkage comprises a first part of the wall, and the second linkage comprises a second part of the wall, the first and second parts of the wall formed by laser-cutting, etching, or removing material from the elongated tube.

11. The medical device of claim 1, wherein the first actuating element comprises a piezo element, a balloon, an electroactive polymer, or a shape-memory element.

12. The medical device of claim 1, wherein the first actuating element is actuatable in response to electrical energy, radiofrequency energy, temperature change, delivery of fluid, or pressure.

13. The medical device of claim 1, wherein the wall of the elongated tube comprises a second opening, and wherein the medical device further comprises a second actuating element located in the second opening of the wall of the elongated tube.

14. The medical device of claim 13, wherein the first actuating element and the second actuating element are located on a same side of the elongated tube.

15. The medical device of claim 13, wherein the first actuating element and the second actuating element are located on different respective sides of the elongated tube.

16. The medical device of claim 13, wherein the first actuating element is configured to cause the elongated tube to bend in a first direction, and the second actuating element is configured to cause the elongated tube to bend in a second direction that is different from the first direction.

17. The medical device of claim 1, wherein the elongated tube is a part of a catheter, a guidewire, or an implant.

18. The medical device of claim 17, wherein the implant is configured to deform plastically.

19. The medical device of claim 1, wherein the first actuating element and/or the elongated tube is configured to deform elastically.

20. The medical device of claim 1, wherein the first actuating element and/or the elongated tube is configured to deform plastically.

21. The medical device of claim 1, wherein each of the first linkage and the second linkage has an elongated configuration.

* * * * *